United States Patent
Oliveira et al.

(10) Patent No.: US 9,993,170 B1
(45) Date of Patent: Jun. 12, 2018

(54) NON-INVASIVE INTRACRANIAL PRESSURE SYSTEM

(71) Applicant: Braincare Desenvolvimento e Inovação Tecnológica LTDA, São Carlos, São Paulo (BR)

(72) Inventors: Sérgio Mascarenhas Oliveira, São Carlos (BR); Gustavo Henrique Frigieri Vilela, Araraquara (BR)

(73) Assignee: Braincare Desenvolvimento E Inovação Tecnológica Ltda, São Carlos, São Paulo (BR)

(*) Notice: Subject to any disclaimer, the term of this patent is extended or adjusted under 35 U.S.C. 154(b) by 0 days. days.

(21) Appl. No.: 15/275,352

(22) Filed: Sep. 24, 2016

Related U.S. Application Data

(62) Division of application No. 13/621,635, filed on Sep. 17, 2012.
(Continued)

(51) Int. Cl.
*A61B 5/03* (2006.01)
*A61B 5/00* (2006.01)
(Continued)

(52) U.S. Cl.
CPC ............ *A61B 5/031* (2013.01); *A61B 5/0205* (2013.01); *A61B 5/11* (2013.01); *A61B 5/4094* (2013.01);
(Continued)

(58) Field of Classification Search
CPC ...................................................... A61B 5/031
See application file for complete search history.

(56) References Cited

U.S. PATENT DOCUMENTS 4,690,149 A    9/1987  Ko
4,971,061 A   11/1990  Kageyama et al.
(Continued)

FOREIGN PATENT DOCUMENTS

CN    101224108 A   7/2008
GB      2156997 A  10/1985
(Continued)

OTHER PUBLICATIONS

PCT, International Preliminary Examining Authority, "International Preliminary Report on Patentability" dated Aug. 1, 2014, for International Ser. No. PCT/IB2012/002550. pp. 1-20.
(Continued)

*Primary Examiner* — Daniel Cerioni
*Assistant Examiner* — Yasmeen S Warsi
(74) *Attorney, Agent, or Firm* — Harness, Dickey & Pierce, P.L.C.

(57) ABSTRACT

Non-invasive intracranial pressure detection and/or monitoring and use of data with respect thereto. Illustratively, with respect to a method, there can be a method to digitally produce and communicate intracranial pressure data from skull deformation electric signals, the method including: receiving, from at least one sensor, detected skull deformation electric signals at electrical equipment configured to transform and process the skull deformation signals that are received; transforming and processing, by the electrical equipment, the received skull deformation electric signals to produce digital intracranial pressure data; and outputting, by the electrical equipment, the digital intracranial pressure data via an output device operably associated with the electrical equipment to render the digital intracranial pressure data.

38 Claims, 24 Drawing Sheets

Related U.S. Application Data

(60) Provisional application No. 61/536,347, filed on Sep. 19, 2011.

(51) Int. Cl.
 *A61B 5/11* (2006.01)
 *A61B 5/0205* (2006.01)
 *A61B 5/024* (2006.01)
 *A61B 5/08* (2006.01)

(52) U.S. Cl.
 CPC .......... *A61B 5/4504* (2013.01); *A61B 5/4538* (2013.01); *A61B 5/4821* (2013.01); *A61B 5/4848* (2013.01); *A61B 5/6803* (2013.01); *A61B 5/7257* (2013.01); *A61B 5/7278* (2013.01); *A61B 5/7282* (2013.01); *A61B 5/743* (2013.01); *A61B 5/746* (2013.01); *A61B 5/7425* (2013.01); *A61B 5/02438* (2013.01); *A61B 5/0816* (2013.01); *A61B 5/4064* (2013.01); *A61B 2503/40* (2013.01); *A61B 2505/09* (2013.01); *A61B 2560/0475* (2013.01); *A61B 2562/0209* (2013.01); *A61B 2562/0223* (2013.01); *A61B 2562/0233* (2013.01); *A61B 2562/06* (2013.01)

(56) References Cited

U.S. PATENT DOCUMENTS

| | | | |
|---|---|---|---|
| 4,984,567 A * | 1/1991 | Kageyama | A61B 5/031 600/438 |
| 5,117,835 A | 6/1992 | Mick | |
| 5,388,583 A | 2/1995 | Ragauskas et al. | |
| 5,617,873 A | 4/1997 | Yost et al. | |
| 5,919,144 A | 7/1999 | Bridger et al. | |
| 6,146,336 A | 11/2000 | Paulat | |
| 6,231,509 B1 | 5/2001 | Johnson et al. | |
| 6,589,189 B2 | 7/2003 | Meyerson et al. | |
| 6,746,410 B2 * | 6/2004 | Yost | A61B 5/031 600/561 |
| 6,761,695 B2 | 7/2004 | Yost et al. | |
| 6,773,407 B2 | 8/2004 | Yost et al. | |
| 7,147,605 B2 | 12/2006 | Ragauskas | |
| 7,775,985 B2 | 8/2010 | Eide | |
| 7,854,701 B2 | 12/2010 | Stergiopoulos et al. | |
| 8,005,686 B2 | 8/2011 | Smith | |
| 8,211,031 B2 | 7/2012 | Poupko et al. | |
| 8,277,385 B2 | 10/2012 | Berka et al. | |
| 9,826,934 B2 | 11/2017 | Oliveira et al. | |
| 2004/0087871 A1 | 5/2004 | Ragauskas | |
| 2006/0100530 A1 | 5/2006 | Kliot et al. | |
| 2008/0200832 A1 | 8/2008 | Stone | |
| 2009/0177279 A1 | 7/2009 | Luciano et al. | |
| 2009/0234245 A1 | 9/2009 | Jaffe et al. | |
| 2010/0161004 A1 | 6/2010 | Najafi et al. | |
| 2010/0198105 A1 | 8/2010 | Avan et al. | |
| 2010/0204589 A1 | 8/2010 | Swoboda et al. | |
| 2011/0060245 A1 | 3/2011 | Piletskiy et al. | |
| 2011/0201961 A1 | 8/2011 | Hu et al. | |
| 2011/0201962 A1 * | 8/2011 | Grudic | A61B 5/021 600/561 |
| 2011/0224570 A1 | 9/2011 | Causevic | |
| 2012/0101387 A1 | 4/2012 | Ji et al. | |
| 2012/0203081 A1 | 8/2012 | LeBoeuf et al. | |
| 2012/0278099 A1 | 11/2012 | Kelly et al. | |
| 2012/0309300 A1 | 12/2012 | Howard et al. | |
| 2012/0330109 A1 | 12/2012 | Tran | |
| 2013/0018277 A1 | 1/2013 | Liu | |
| 2013/0041271 A1 | 2/2013 | Ben-Ari et al. | |

FOREIGN PATENT DOCUMENTS

| | | |
|---|---|---|
| WO | WO-1992002174 A1 | 2/1992 |
| WO | WO-2010056401 A1 | 5/2010 |

OTHER PUBLICATIONS

PCT, "International Search Report" dated May 15, 2013, for International Ser. No. PCT/IB2012/002550. pp. 1-2.

PCT, International Preliminary Examining Authority, "International Preliminary Report on Patentability" dated Mar. 25, 2014, for International Ser. No. PCT/IB2012/002550. pp. 1-19.

PCT, International Preliminary Examining Authority, "Written Opinion of the International Searching Authority" dated May 15, 2013, for International Ser. No. PCT/IB2012/002550. pp. 1-18.

Bozena Smagowska and Malgorzata Pawlaczyk-uszczy ska. "Effects of Ultrasonic Noise on the Human Body—A Bibliographic Review" International Journal of Occupational Safety and Ergonomics (JOSE) 2013, vol. 19, No. 2, 195-202.

EPO, "European Search Report" dated May 8, 2015 for EP Serial No. 12833644.3.

* cited by examiner

NON-INVASIVE INTRACRANIAL PRESSURE SYSTEM

The present patent application is a division of, and incorporates by reference as if fully restated herein, U.S. patent application Ser. No. 13/621,635, filed Sep. 17, 2012, pending. U.S. Ser. No. 13/621,635 claims benefit from and incorporates by reference U.S. Patent Application Ser. No. 61/536,347, filed on Sep. 19, 2011.

I. TECHNICAL FIELD

The technical field includes machine, manufacture, article, process, and product produced thereby, as well as necessary intermediates, which in some cases, pertains to non-invasive intracranial pressure detection and/or monitoring and use of data with respect thereto.

II. SUMMARY

Depending on the implementation, there is apparatus, a method for use and method for making, and corresponding products produced thereby, as well as data structures, articles, computer-readable media tangibly embodying program instructions, manufactures, and necessary intermediates of the foregoing, each pertaining to non-invasively detecting and/or monitoring intracranial pressure, e.g., in animals, humans, which may be in ex-vivo and/or in-vivo conditions.

III. FIGURES

IV. MODES

Intracranial Pressure (ICP) is the relation between the volume of the intracranial space and its components: Cerebral spinal fluid (CSF), blood and brain parenchyma. ICP monitoring can be used in the diagnosis and prognostics of various disorders such as neurological disorders, e.g., stroke, hydrocephalus, tumors well as trauma. Rather than using an invasive technique, i.e., requiring shaving, incision in the patient's head, trepanation of the skull bone and sensor insertion in the brain tissue, embodiments herein involve noninvasive embodiments, e.g., for monitoring this medical parameter, through the cranial bone.

Generally, there can be at least one sensor located to detect intracranial pressure noninvasively, in contrast to being directed to a sensor located invasively, e.g., within a skull or under the skin or where the skin has been removed, e.g., by incision. (The following discussion refers to "sensor" in the singular, with the understanding that embodiments can be configured with one or more sensors.) The sensor can be located with a strap, as an example of a non-invasive manner of locating the sensor with respect to the subject's head. In some embodiments, the sensor can be detecting intracranial pressure by a spring located between the sensor and the patient's head. In any case, the sensor detects intracranial pressure with signals that can be communicated to equipment. Equipment processes the received signals as signal data. That is, if the signals are analog signals, they are converted to digital signal data. In any case, the signal data is saved to a memory configured to store the signal data. The signal data can be processed and also saved in memory configured to store the processed signal data, and can be rendered at a display.

The embodiments can be such as to non-invasively detect and/or monitor what is happening directly inside the central nervous system, e.g., in the patient's head, for such variables otherwise not known to be observable without invasive methods. The central nervous system observations are unique because of the many physiological barriers such as blood-brain-barriers of complex nature containing biochemical, electrophysiological and other components. Peripherical measurements of the arterial or venous pressure or haemodynamic variables normally used in present medical procedures do not necessarily correspond to the corresponding variables monitored by embodiments herein described.

Figure 1:
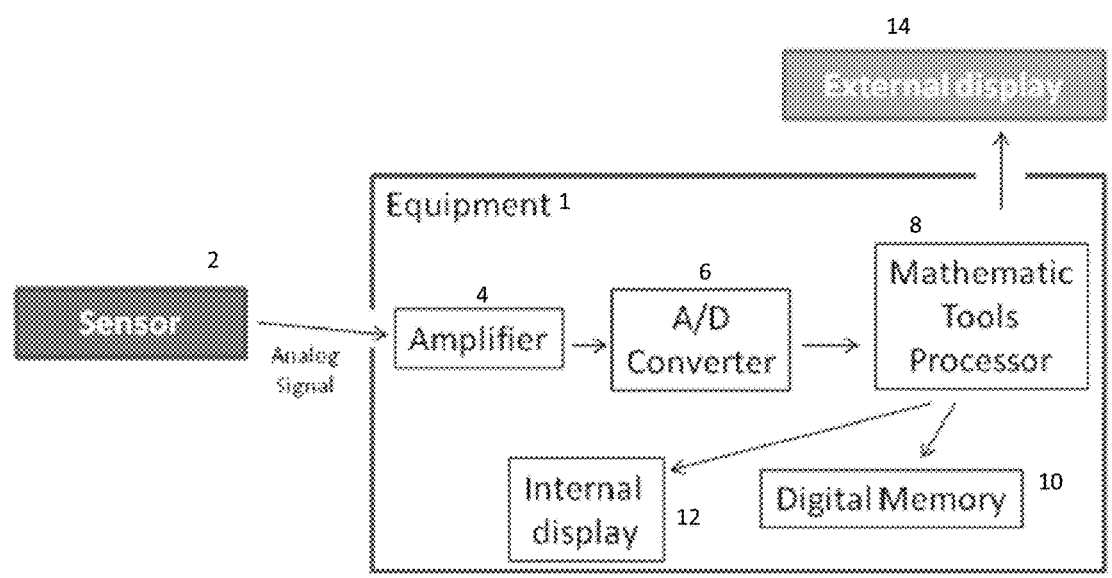
FIG. 1 is an illustrative architecture for embodiment with respect to intracranial pressure monitoring system.

The accompanying figures and discussion of embodiments are intended to illustrate and exemplify in a teaching manner, by way of the prophetic teachings. With this in mind, turn to FIG. 1 and consider that equipment 1 can include sensor device 2 can non-invasively located adjacent and proximate to the head of a subject, such as a human "patient". Sensor device 2, can be located, for example, so as to allow movement by the patient, e.g., with a strap 3. In another embodiment, sensor device 2 can be located, for example, so as to immobilize the patient or in a helmet.

In some embodiments, the sensor device 2 can detect skull deformation by such as by an electric strain gage, an optical sensor, an optical fiber, a magnetic sensor, an interferometric sensor, or any other device which detects and/or monitors the skull deformation without trichotomy or surgical incision. Sensor device 2 can, but need not, be configured to be disposable or reusable after use by the patient in a detecting session.

Generally, equipment 1 associates the skull deformation with intracranial pressure detection and changes. Equipment 1 can, but need not, include a signal amplifier 4 to amplify signals received from sensor device 2. Equipment 1 can, but need not, include an analog to digital converter 6. That is, if an analog implementation is carried out, there can be a conversion of the analog signals into digital signals, e.g., signal data. Equipment 1 can be powered by regular utility electricity, e.g., an AC power source, or by battery power, e.g., to allow and/or protect monitoring during a power failure or to under conditions where regular electrical utilities are unavailable, e.g., in an ambulance. The equipment 1 has a capability of receiving signals from at least one, and in some embodiments, multiple sensors, and working with different acquisition frequencies.

Equipment 1 can include a processor 8, e.g., in a multi-parametric monitor, computer, etc, which processes the signal data to produce output data that is stored in memory operably associated with the processor 8, e.g., a digital memory 10. The digital memory (device) 10 can have a database configured to store the signal data and/or the output data. The signal data and/or the output data can be rendered on an internal display 12 and/or on an external display 14.

The equipment 1 can be configured so that an intracranial pressure apparatus, whatever be the implementation desired, produces output which can include real-time curves of physiological parameters such as intracranial pressure, respiratory and cardiac cycles, and the like on an internal display 12 and/or an external display 14. The equipment 1 can save the data the patient's time series, e.g., for subsequent review and/or processing, in memory 10.

Figure 2:
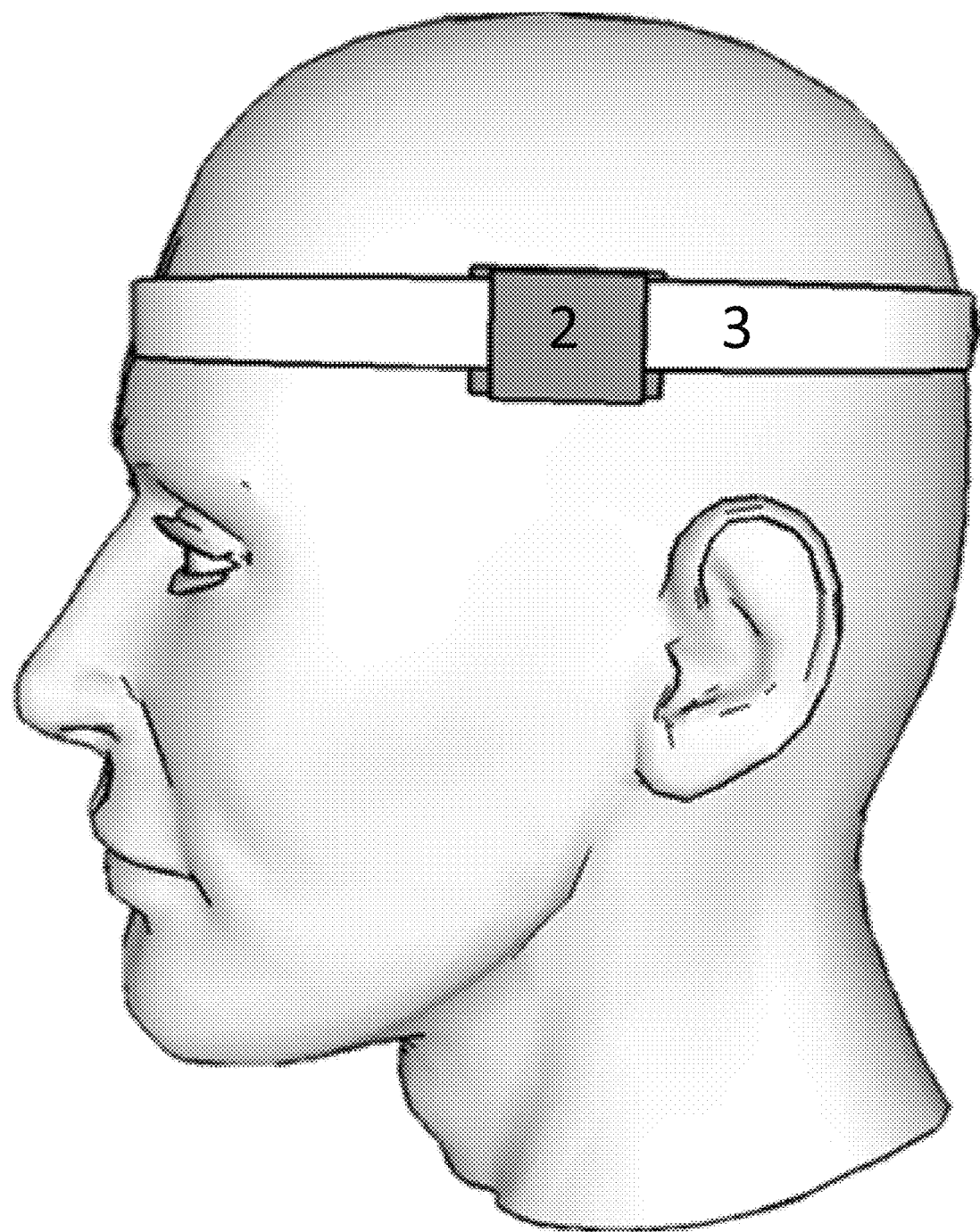
FIG. 2 is an illustrative embodiment including a brain strap with a corresponding sensor housing, oriented to a human patient's head.
Figure 3:
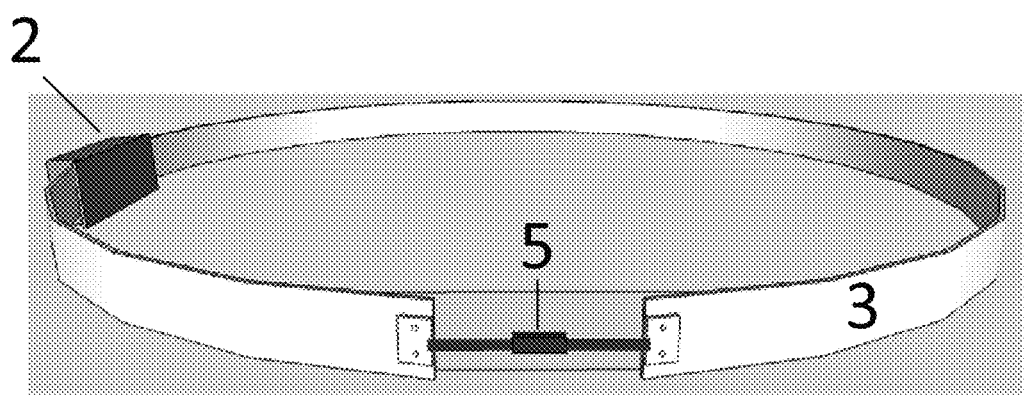
FIG. 3 is an illustrative embodiment of a strap with a sensor housing and an adjustment means.

Consider now the embodiment illustrated in FIGS. 2 and 3, wherein a non-invasive sensor device 2 for detecting or monitoring ICP includes a sensor device 2, which is configured to provide protection and location for at least one ICP monitoring sensor (not shown in FIG. 2). The sensor device 2 can be attached to the patient's head with a strap 3 which can be produced, for example, from an elastic or rigid material and configured to provide dimensional adjustment to the patient's head.

The strap 3 can be coupled to the sensor device 2 through fittings or other means, e.g., at both ends, such as direct affixing in an upper portion of the sensor housing (FIG. 3). The strap 3 can locate one or more of sensor device 2. The strap 3 can, but need not, include an adjustment system 5.

Helmets, hoods, or arcs may instead be used to affix a sensor device 2 with respect to the patient's head, or other means can be used to provide an equivalent function as the strap 3.

Figure 4:
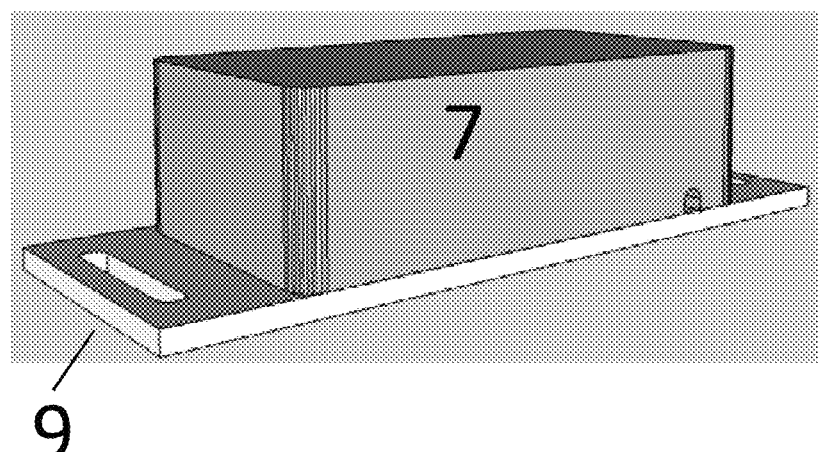
FIG. 4 is an illustrative embodiment of the housing for the sensor.
Figure 5:
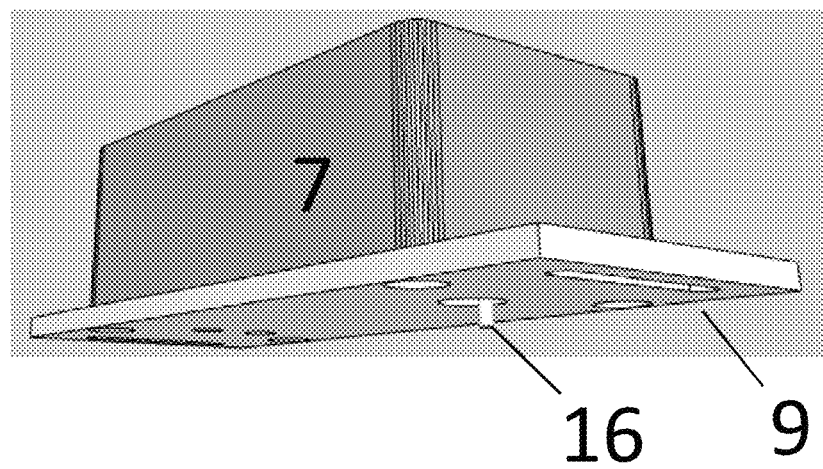
FIG. 5 is another illustrative embodiment of a housing for a sensor.
Figure 6:
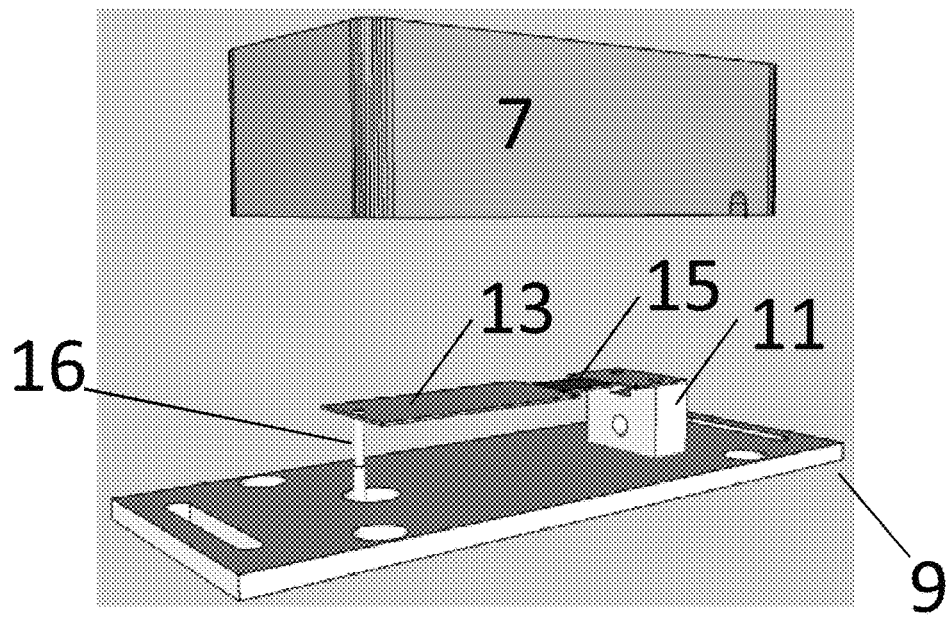
FIG. 6 is another illustrative embodiment of components within the housing.
Figure 7:
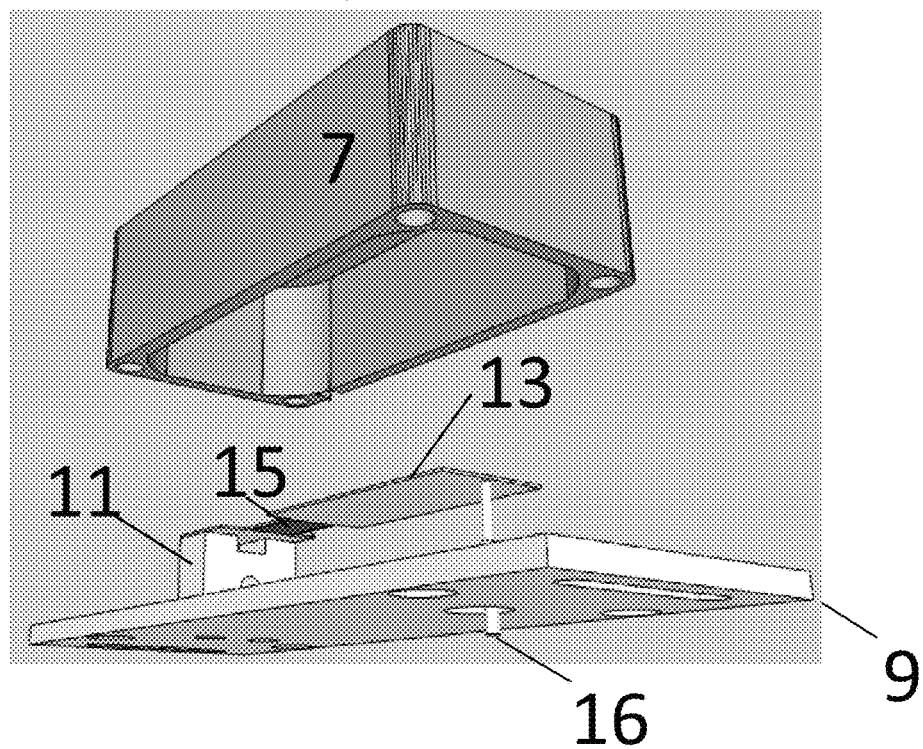
FIG. 7 is another illustrative embodiment of the components within the housing.
Figure 8:
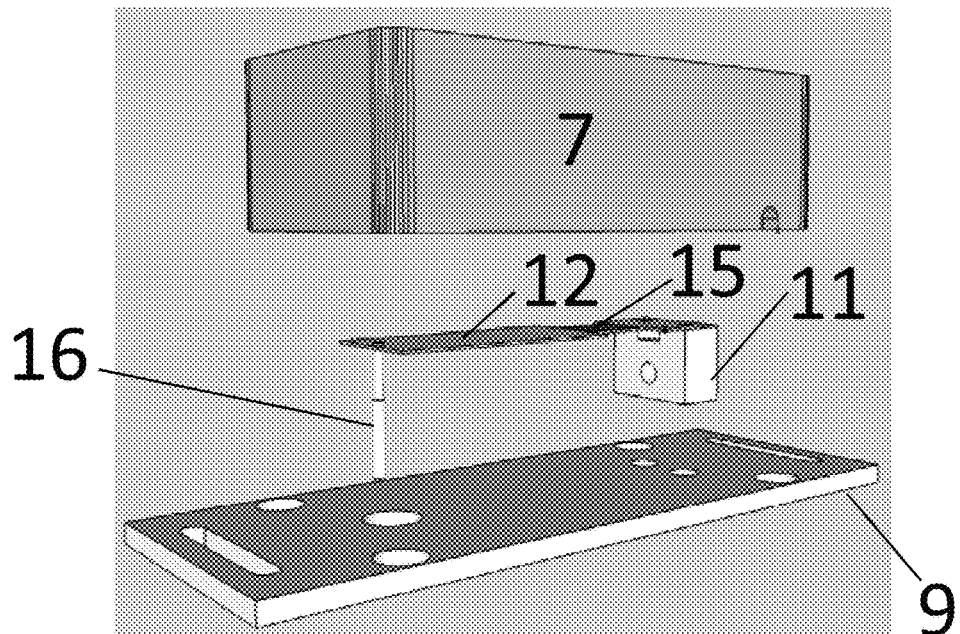
FIG. 8 is another illustrative embodiment of the components within the housing.
Figure 9:
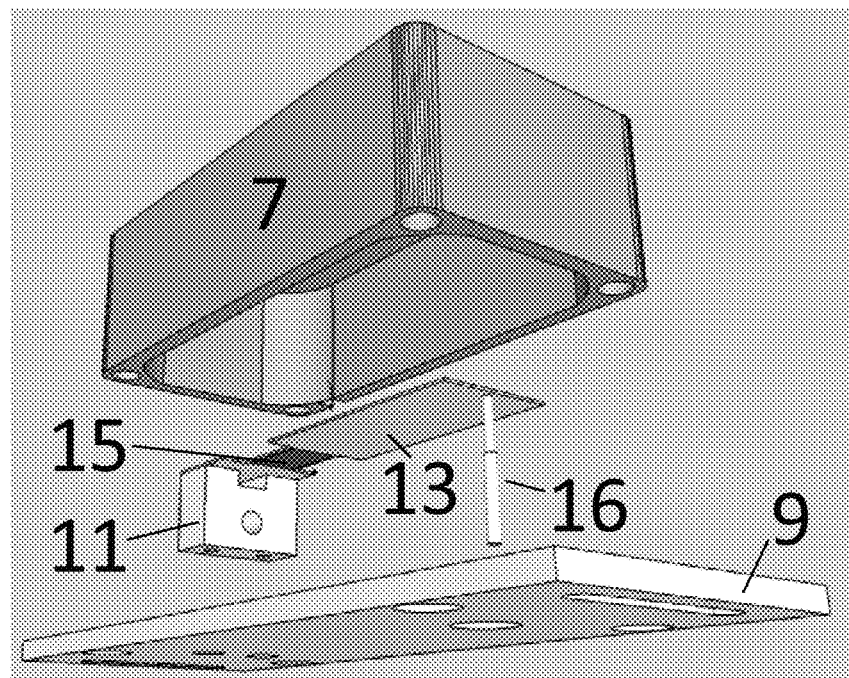
FIG. 9 is another illustrative embodiment of the components within the housing.
Figure 10:
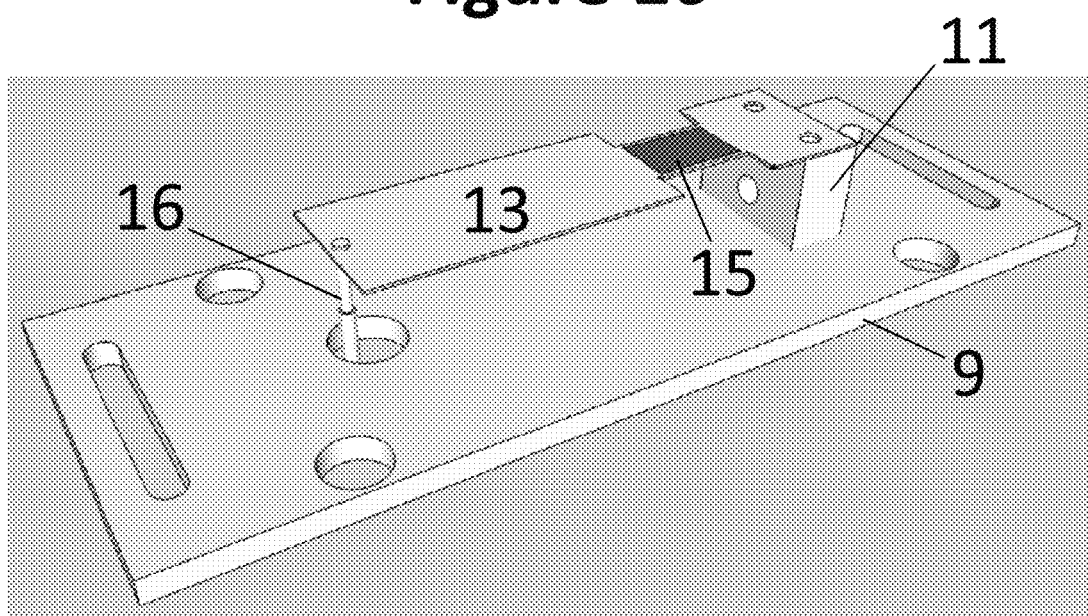
FIG. 10 is another illustrative embodiment of the components within the housing.

In the illustration of FIG. 4, there can be a sensor housing comprising a lid 7 and a sensor box base 9. Attached to the base 9, there can be a support 11 for a sensor bar 13, adapted for stabilizing and affixing the strain sensor 15 with respect to the base 9.

At an end of sensing bar 13 (opposite the support 11) there can be a pin 16 configured for contacting the patient's head. This pin 16 can be fixed to bar 13 to communicate changes in skull volume to sensor 15.

Components such as 7, 9, 11, 13, and 16 can be produced out of metal, polymer, carbon, glass fibers, and any combination thereof.

Alterations in ICP cause changes in cranial volume, detected by pin 16. The pin 16 of the sensor 15 contacts the surface of the patient's head, to detect variations in the volume of the skull. Pin 16 causes a deformation in, or communicated by, bar 13, and the deformation is captured by the sensor 15 adjacent to an opposite end of the bar 13. Accordingly, the device 2, and methods of its use, can be used to detect and/or monitor ICP in humans or animals, even in diverse situations, such as trauma, hydrocephalus, intracranial tumors, stroke, pharmacological studies, etc.

So in the illustrated embodiments illustrated in FIGS. 2-12, there can be one or more noninvasive sensor devices 2, a strap 3 or the like, and equipment 1, which can is communicatively arranged with the sensor 15, e.g., via wires, wireless communication technologies, etc. The equipment 1 filters and amplifies signals from sensor 15, may in some embodiments digitalize the signal from the sensor 15, and can send the signal or other output to a printer, computer, tablet, mobile phone, medical monitor, its own display 12, etc. There can be a digital memory 10 in equipment 1, e.g., a memory card, to store the digital data, allowing for later analysis.

Figure 28:
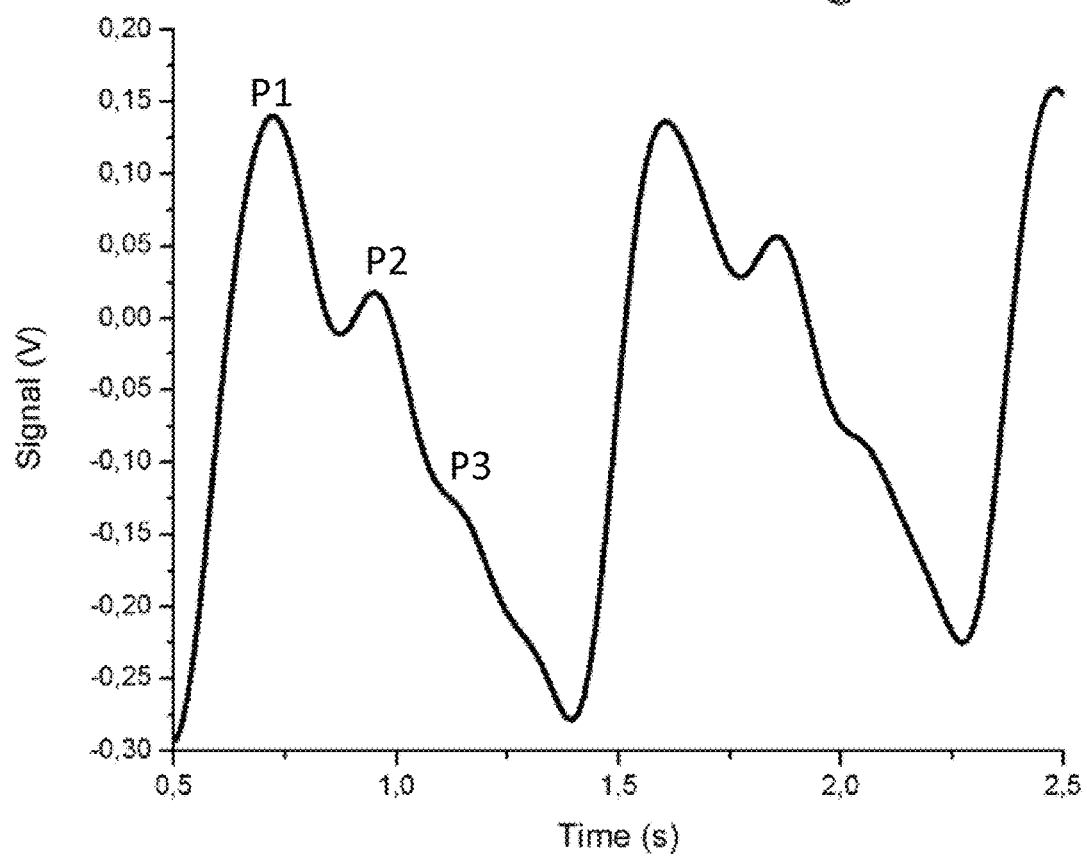
FIG. 28 is an illustrative ICP waveform monitored with the ICPNI monitor.

The noninvasive monitor can facilitate adjusting equipment 1 for sensitivity to acquire the characteristic morphology of intracranial pressure waves, with their peaks P1, P2, and P3 (FIG. 28). The sensor 15 used may, for example, be a full-bridge, a quarter-bridge, or half-bridge sensor, presenting values of electrical resistance in a system detecting ICP.

FIG. 2 illustrates a brain strap embodiment in which the sensor device 2 is non-invasively contacting a surface of a patient's head, proximate to the skull bone, with a band 3. The strap and/or band can, but need not, be configured to be disposable than be reused after use by the patient in a detecting session. In such an embodiment, the band 3 can be of a material that is non-rigid, such as a polymer or metallic, for example, foil, strip, tape, or the like. Sensor device 2 can be attached to, or positioned with respect to, the material and the patient's head so as to allow for detection of ICP.

In such embodiments, there can be a connector, such as a wire or other means (not shown in the Figures), communicating the signals from the sensor device to the equipment 1. (In other embodiments, the sensor device(s) can be communicatively associated with the equipment 1 by Bluetooth, ZigBee, or any other remote communication systems.)

Note that a configuration fixes the sensor 15 and sensor device 2 on the patient's head, without trichotomy or surgical incision, allowing his or her (or its) movement during the intracranial pressure detecting and monitoring.

Figure 11:
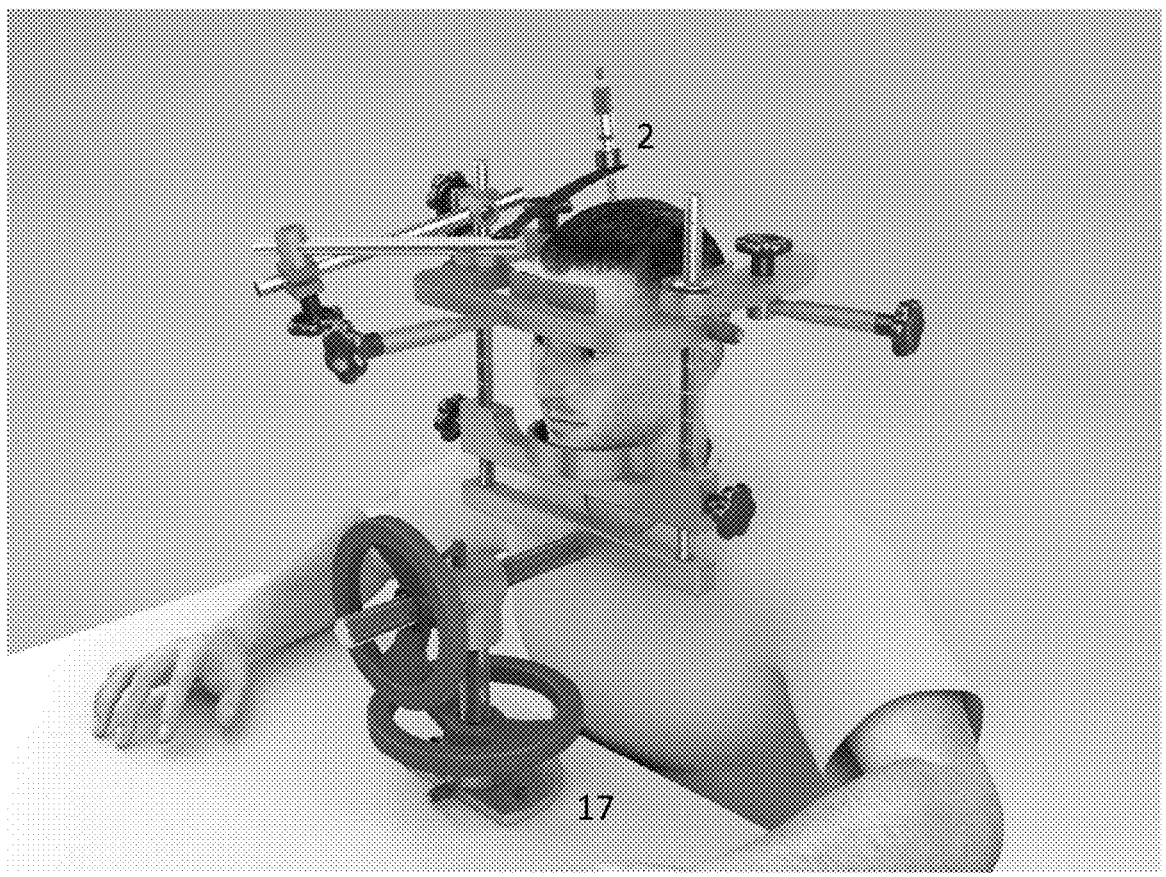
FIG. 11 is an illustrative embodiment including a brain helmet with a corresponding sensor.
Figure 12:
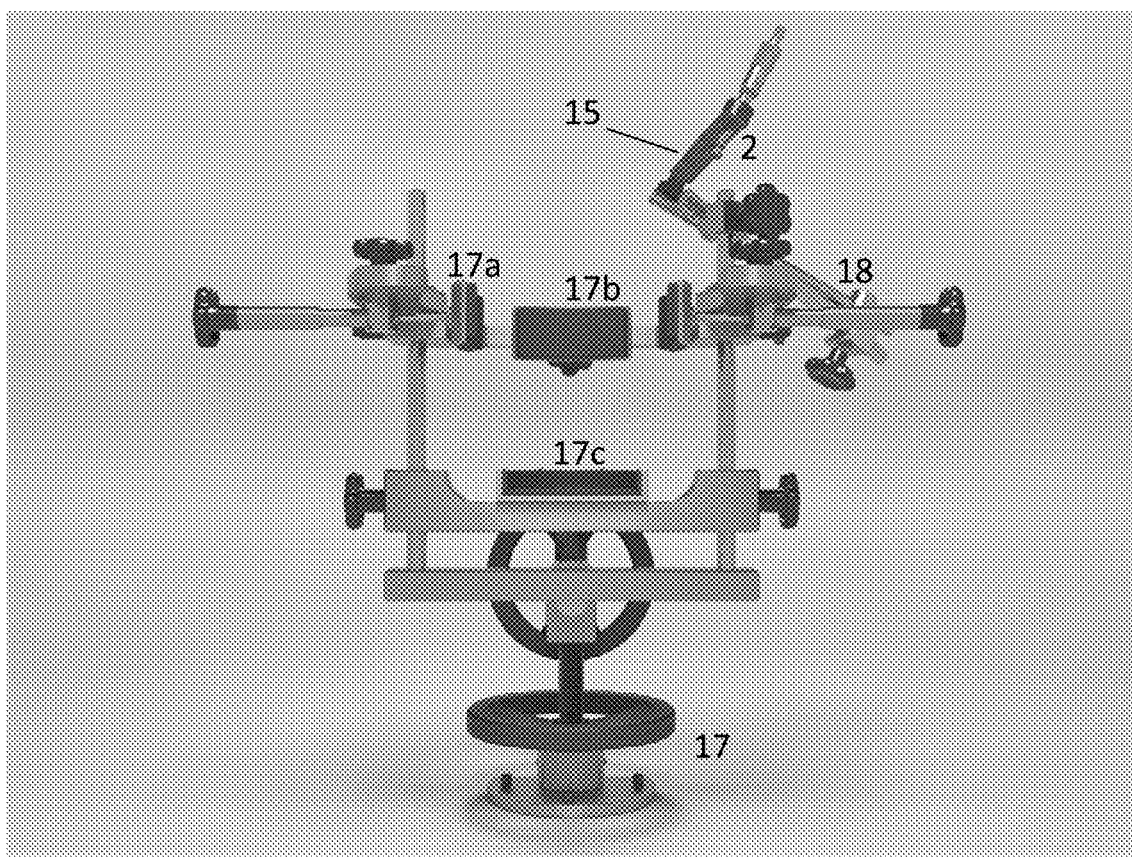
FIG. 12 is another illustrative embodiment of the brain helmet.

FIG. 11 and FIG. 12 illustrate more of a helmet-type embodiment in which the sensor 15 is non-invasively contacting a surface of a patient's head, proximate to the skull bone, with a helmet device 17. Device 17, e.g., with a stereotaxic apparatus, can be such as to immobilize the head of the patient with respect to the sensor device 2 in a fixed position contacting with the surface of the patient's head. One may, but need not, use such a configuration where certain patient movement is not of particular interest, or for reproducibility of detecting and/or monitoring a condition where position is held constant. In such an embodiment, there can also be a portion of a strap 3, with the sensor device 2, that can, but need not, be configured to be disposable rather than be reused after use by the patient in a detecting session.

As illustrated more particularly in FIG. 12, device 17 can be a stereotaxic apparatus to fix the patient's position geometrically in the system (17a—support for temporal regions, 17b—support for forehead, and 17c—support for the chin). In some such embodiments, there can be quantitative numerical marks on the bars that regulate the supports (17a, 17b, and 17c) for reference. As illustrated by comparison of FIGS. 11 and 12, the device 17 can comprise movable arms 18 that locate the patient, or in another way of thinking the sensor 15, with respect to each other.

The strap embodiments, or the more helmet-type embodiments, can use the flexible material approach discussed above, e.g., such as foil, with a (e.g., strain gage) sensor 15, e.g., configured in connection with device 17. Another approach is to use a sensor 15 with a spring (see FIGS. 13 and 14), e.g., in a housing 20.

Figure 13:
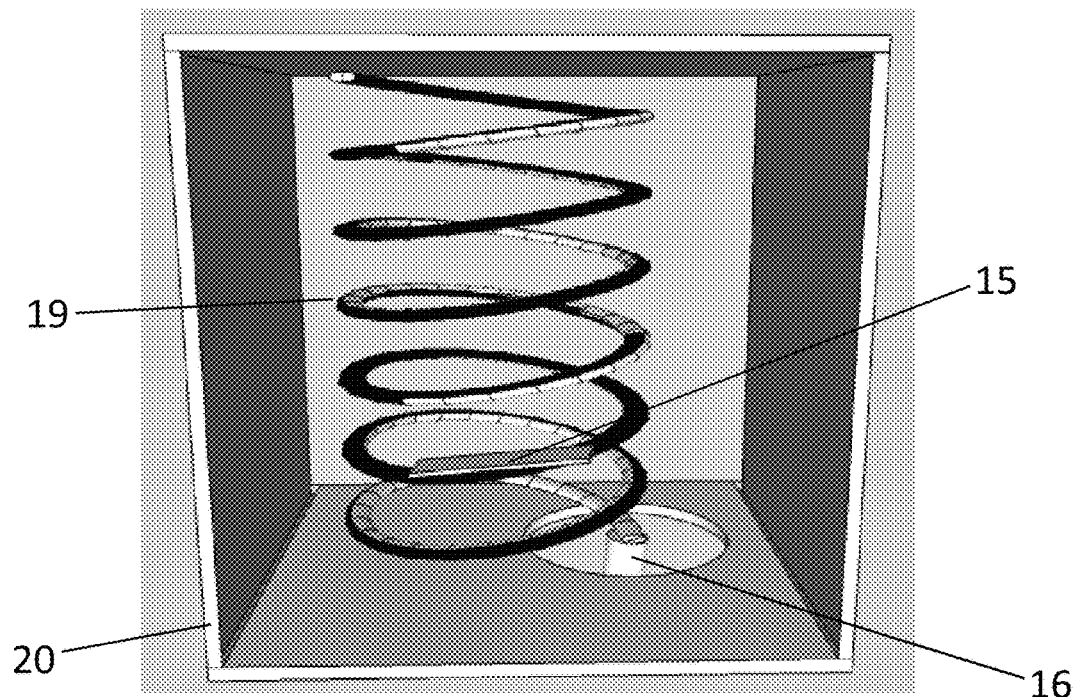
FIG. 13 is an illustrative embodiment of a spring configuration.
Figure 14:
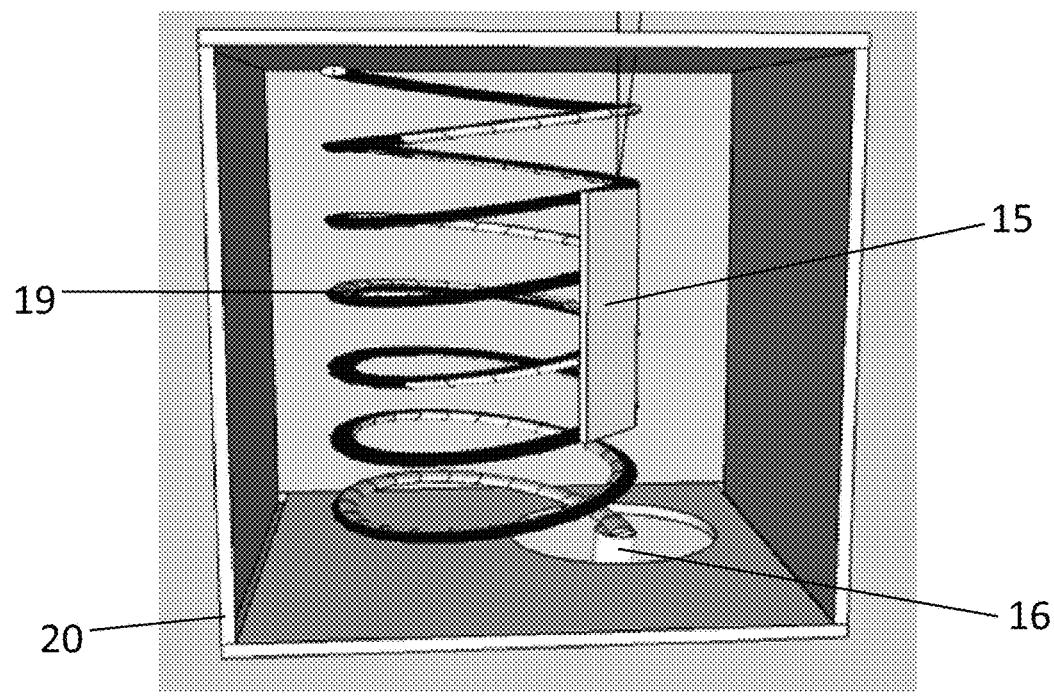
FIG. 14 is an illustrative of another embodiment of a spring configuration.

Turning to FIGS. 13 and 14, the noninvasive sensor can use one or more springs 19 in detecting the intracranial pressure. One end of the spring 19 can be adjacent to an upper end of housing 20. A pin 16 is urged by the spring 19 into contact with the head of the patient. FIGS. 13 and 14 show various configurations of the noninvasive sensor 15 in communication via the spring 19 with a pin 16 locatable into contact with the patient's head.

There can be various embodiments hereinafter. In one embodiment, the output or raw data can also be stored and rendered via polygraph system.

Illustratively, embodiments can be carried out by such as the following.

In one embodiment, the equipment 1 can be used, for example, with the brain strap sensor approach, by:

1—Placing the sensor 15 tip 16 over the adequate region of the skull bone, for instance the parietal bone region;

2—Using an elastic strap 3 to fix the sensor device 2 on the head of the patient, e.g., as shown in FIG. 2;

3—Connecting the sensor device 2 to the equipment 1 using wires (or connecting by wireless protocols);

4—Commencing detection and/or monitoring procedure to obtain intracranial pressure signals:

5—Processing, including by a processor 8, the intracranial pressure signals to produce intracranial pressure data;

6—Storing the intracranial pressure data in a database configured to store the intracranial pressure data, the database in a memory 10 operably associated with the processor 8; and 7—Displaying 12/14 the intracranial pressure data.

In some embodiments, there can be such as:

1—Communicating signals from the sensor 15, i.e., a full detected signal, to the equipment 1, the full signal can be a sum of cardiologic, respiratory, ICP signals—and others, if so desired;

2—Receiving, the full signal (e.g., in microvolts) at an amplifier 4 and amplifying the microvolts to volts (1000×);

3—Converting, by an analog-to-digital converter 6, the analog signal into a digital data;

4—Processing the digital data with such as mathematical analyses to produce output;

5—Storing the digital data and at least some of the output in the database;

6—Rendering the output or communicating it to be output, to a display 12/14.

With respect to the processing, the equipment 1 can carry out mathematical processing, such as Fourier Transform, to separate the signals, which can then be stored and rendered, e.g., via an output device such as a printer and/or display 12/14. In some embodiments, the equipment 1 renders signals such as the filtered signal via an output device, such as a multiparametric monitor, printer, computer or monitor, computer-to-computer communication device, such as a router or gateway.

Figure 15:
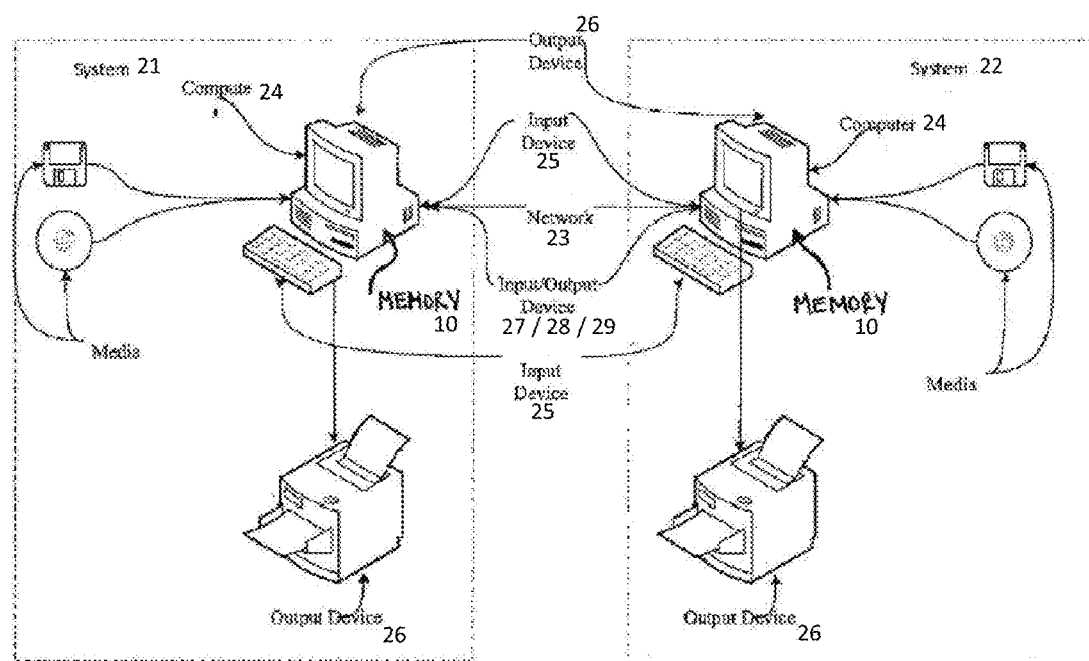
FIG. 15 is an illustrative embodiment of a computer system.

As mentioned above, in other embodiments, equipment 1 has a processor 8, and in some but not all embodiments, the processor 8 can be a processor (a processor can be multiple processors working in cooperation) of a computer system as is illustratively represented in FIG. 15. In another configuration, a computer system can be operably associated or in communication with a processor 8 of a multiparametric monitor, and either or both can be in communication with another computer system.

More particularly, by way of example, there can be a computer system 21, which in some embodiments can include processor 8 and in other embodiments can receive data from equipment 1. In either case, computer system 21 can interact with another computer system 22, via a network 23. As used herein, the term "computer" generally refers to hardware or hardware in combination with one or more program(s), such as can be implemented in software. Computers can be implemented as general-purpose computers, specialized devices, or a combination of general-purpose and specialized computing devices. Computing devices can be implemented electrically, optically, quantumly, biologically, and/or mechanically or in any combination of these technologies. A computer as used herein can be viewed as at least one computer having all functionality or as multiple computers with functionality separated to collectively cooperate to bring about the functionality, e.g., the functions shown as being carried out by a single computer can be carried out by more than one computer, and the functions shown as being carried out by more than one computer can be carried out by a single computer, without departing from the present intent. In some, but not all embodiments, the computer 24 can include a single processor, such as processor 8 and/or multi-processor 8 implementations of a computer. A processor 8 can include any device that processes information or executes instructions. Computer logic flow and operations can be used in processing devices, including but not limited to: signal processors, data processors, microprocessors, and communication processors. Logic flow can be implemented in discrete circuits, combinational logic, ASICs, FPGAs, reconfigurable logic, programmed computers, or an equivalent.

Computer-readable media or medium, as used herein, includes any technology that includes a characteristic of memory, e.g., tangibly embodying a program of instructions executable by a computer to perform operations according to an embodiment herein. Memory technologies can be implemented using magnetic, optical, mechanical, or biological characteristics of materials. Common examples of memory are RAM, ROM, PROM, EPROM, FPGA, and floppy or hard disks. Communications medium or connection, as used herein, is any pathway or conduit in which information can be communicated or exchanged. The pathway or conduit can be wired, optical, fluidic, acoustic, wireless, or any combination of the foregoing.

A "computer" or "computer system(s)" as used herein can include one or more computers, which illustratively can be PC systems, server systems, mobile devices, and any combination of the foregoing. Depending on the implementation, a computer can be adapted to communicate among themselves, or over a network such as the Internet. Programs, as used herein, are instructions that when executed by a processing device causes the processor to perform specified operations. Programs can be written in various languages, including but not limited to assembly, COBOL, FORTRAN, BASIC, C, C++, Java, or JavaScript. Languages can be object-oriented like C++ and Java, for example. The programming language can be interpreted or compiled, or a combination of both. The programs are usually processed by a computing system having an operating system. An operating system can be processor-specific, like an RTOS (real time operating system) used in cell phones, or commercial like Mac OS X, UNIX, Windows, or Linux. An operating system or program can be hardwired, firmware, reside in memory, or implemented in an FPGA or reconfigurable logic.

A "network" as described here can be a preconfigured network, like a local area network ("LAN") of computers, servers, and peripheral devices in a single office, or an ad hoc network caused by the temporary interconnection of computers over the Internet, by modem, via telephone, cable television, radio communication, combinations of these (like a telephone call made in response to a television solicitation), or otherwise to conduct a particular transaction. In the latter sense, the computers in the network do not need to all be linked up at once; as few as two of them can be linked at a time. The link can be a formal link or a casual link, as by sending e-mails or other communications from one computer to the other, or logging one computer into a website maintained on another via the Internet.

The network or Internet-type network connections or communication paths described above can be made in various ways. In one embodiment, the Internet connection can be enabled by a series of devices and transmission lines or paths including: a first computer; a modem connected to the first computer; a telephone (regular or DSL) or cable television transmission line or radio communication channel connected with or generated by a transmitter associated with the modem; a first Internet Service Provider (ISP) receiving the communication; the Internet, to which the first ISP is connected; a second ISP connected to the Internet, receiving the communication; a telephone or cable television transmission line or radio communication channel connected with or generated by the ISP; a modem connected to the second computer; and the second computer.

For example, a computer system 21 and/or 22 can each comprise a computer 24 (e.g., a Lenovo, HP, Apple, or other personal computer; an enterprise server computer; distributed computing; etc.) with one or more processors 8 (e.g., an Intel or AMD processor or the like), memory 10 (e.g., RAM, a hard drive, disk drive, etc.) not shown in FIG. 15, one or more input devices 25 (e.g., keyboard, mouse, modem, sensor 15, e.g., via amplifier 4 and analog to digital converter 6 or the like (see FIG. 1)), and one or more output devices 26 (e.g., a modem, a printer, a display 12 monitor, external display 14, and/or other such output devices). Note that a gateway 27 or modem 28 or router 29 are each illustrative of a computer-to-computer communication device that can operate as an input/output device. To provide other illustrative embodiments, the computer system(s) 21/22 can comprise at least one of a desktop computer, a telephonic device, a console, a laptop computer, a tablet, and a mobile communication device. The mobile communication device can comprise at least one of a cellular telephone, laptop, a PDA, and a smartphone-type device such as an iPhone. Communications between devices may be wired (e.g., cabled Ethernet home or office network), wireless (e.g., IEEE 802.11 A/B/G/N network transceivers), or near-field radio-frequency communications (e.g., Bluetooth), or optical (e.g., infrared). Networking between devices may be through WANs, LANs, Intranets, Internet or peer-to-peer arrangements, or in a combination of them. The network 23 may include, for example, gateways, routers, bridges, switches, front-end and back-end servers, ISPs (Internet Service Providers), which may interact with content provider servers, scanners, copiers, printers, and user computing devices. Devices on the network may include interfaces that can be simple, such as a keyboard with an LCD screen, or can be complex, such as a web interface. Web interfaces are presented in a web browser environment. Web browsers render XML or HTML containing pictures, video, audio, interactive media, and links in the display of a computer. Firefox, Internet Explorer, Safari, Chrome, and Opera are examples of well-known web browsers that are available for PCs and mobile devices. Network 23 can be the Internet.

Figure 16:
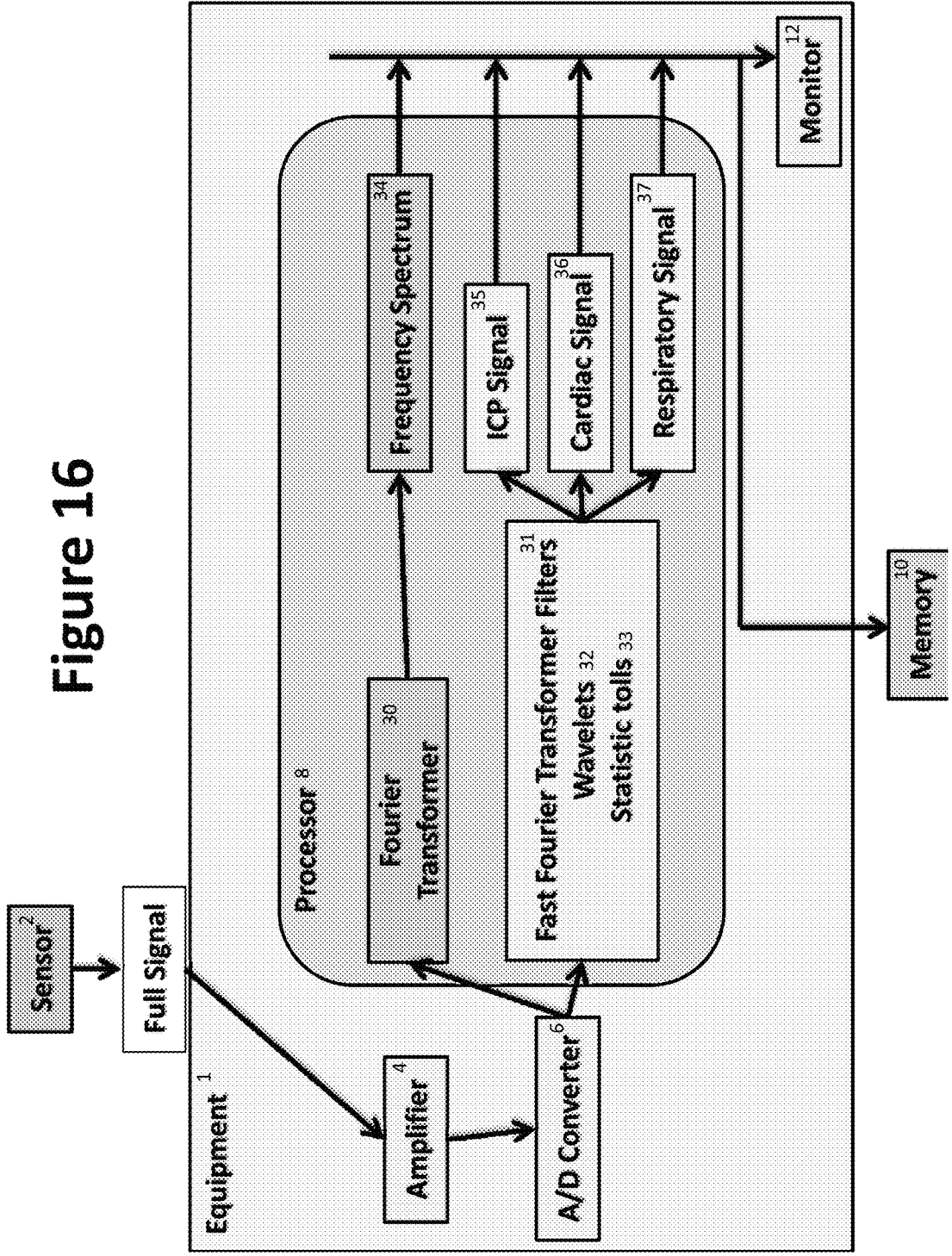
FIG. 16 is an illustrative embodiment of logic flow.

FIG. 16 illustrates, again in a teaching rather than in a limiting manner, logic flow of at least one computer system configured to carry out an embodiment. In the embodiment illustrated, not in a limiting manner, sensor 15 provides a full signal to amplifier 4 which amplifies the full signal to produce an amplified full signal. The amplified full signal is communicated to analog-to-digital converter 6, which converts the amplified full signal to produce signal data. The signal data is communicated to processor 8, which can process and transform the signal data, e.g., by applying a Fourier Transform 30 and/or Fast Fourier Transform filters 31, wavelets 32 and/or statistical tolls 33. Fourier filters decompose a sequence of values into components of different frequencies, for example, most people present a heart rate between 50 and 120 bpm, and these filters can detect the signals in this frequency range and exhibit such as heartbeat signals. The filters can, but need not, be such as origin, matlab, qtiplot, or other signal analysis filter, some of which may use methods such as fast fourier transforms, wavelet processing, and statistical methods for signal analysis and interpretation. The filtering can be carried out to display, or to isolate, physiological components such as cardiologic, respiratory and intracranial pressure data.

The signal data is processed or transformed by the Fourier Transform 30 to produce a frequency spectrum data 34. The signal data is processed or transformed by the Fast Fourier Transform filters 31, wavelets 32 and/or statistical tolls 33 to separate out and produce intracranial pressure signal data 35, cardiac signal data 36, and respiratory signal data 37.

The frequency spectrum data 34, intracranial pressure data 35, cardiac data 36, and respiratory data 37 are communicated to memory 10 and display 12 and/or 14 and/or other output device. Memory 10 includes a database configured to store the frequency spectrum data 34, intracranial pressure data 35, cardiac data 36, and respiratory data 37. In some, but not all, embodiments, computer system 21 associates or further processes some or all of data 34, 35, 36, and 37, into further output, e.g., which can in some embodiments be communicated as illustrated in FIG. 15 from computer system 21 to computer system 22, either of which can further process or transform some or all of the output received so as to produce yet further output.

So for example, though not illustrated in FIG. 15, in some but not all embodiments, the equipment 1 is used to produce output which is then inserted by at least one of computer systems 21 and 22 into a report (or other document), such as a medical record. The report or medical record can be generated and configured so that some or all of data 34, 35, 36, and 37 is located contextually into the report or medical record, which can then be stored e.g., in computer-readable memory, displayed electronically, communicated over a network, or output in hard copy at an output device, e.g., printer. The report or medical record can be generated so that some or all of data 34, 35, 36, and 37 is located in a preconfigured location in the report or medical record and associated, by at least one of computer systems 21 and 22 with other data. So for example, the report can be generated and configured such that some of data 34, 35, 36, and 37 is electronically located in the report or medical record in association with data one or more of neurological, physiological, pharmacological, endocrinological data, obtained from a memory, such as memory operably associated with at least one of computer systems 21 and 22, e.g., having been previously input. In some embodiments, computer system 21 or 22 is programmed to request and capture patient data (e.g., name, age, identification of the patient, hospital registration number, pathology(ies), and other such data in forming, or combining the data 34, 35, 36, and 37 into the report or medical record.

Figure 17:
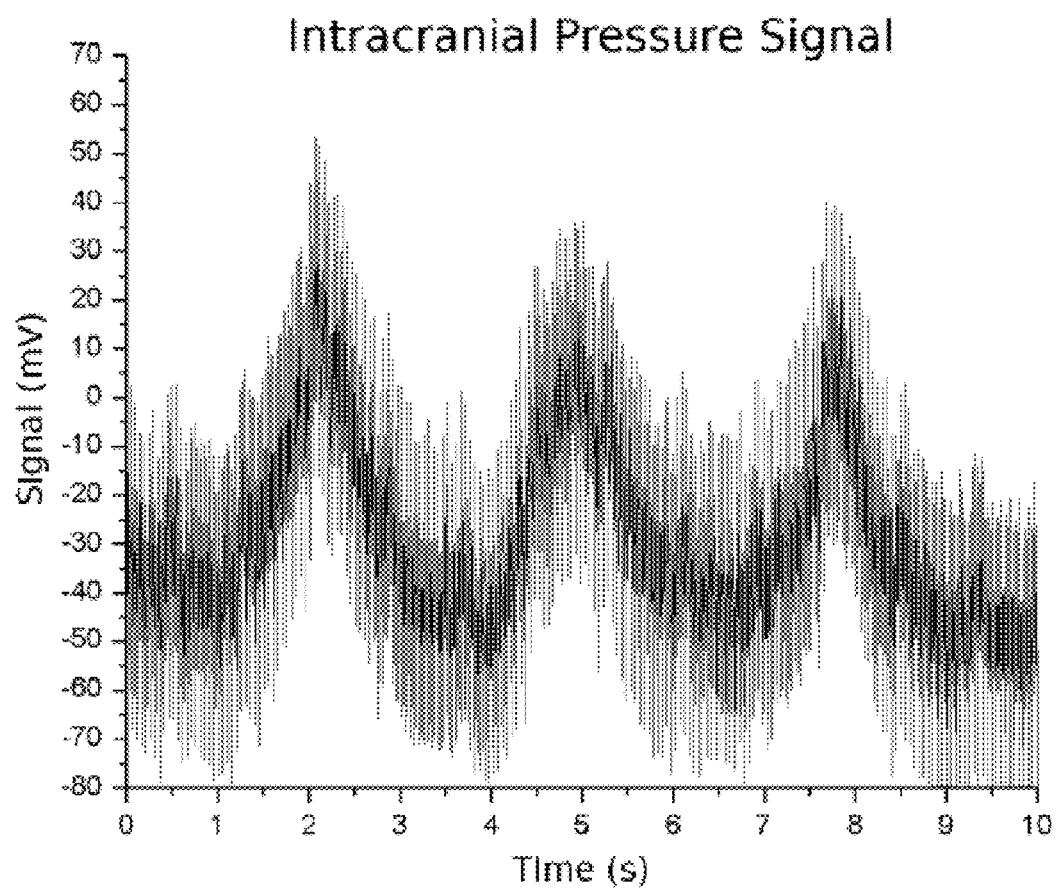
FIG. 17 is an illustrative embodiment of an intracranial pressure signal.

FIG. 17 illustrates the output at, e.g., display 12 and/or 14. The illustrated output is the signal data, e.g., prior to the Fourier Transform 30 or the Fast Fourier Transform Filters 31. The signal data shows raw digital signal data of intracranial pressure. The display shows the full signal from the sensor 15, i.e., the ICP signal, the respiratory signal and frequency, and the cardiac signal and frequency.

Figure 18:
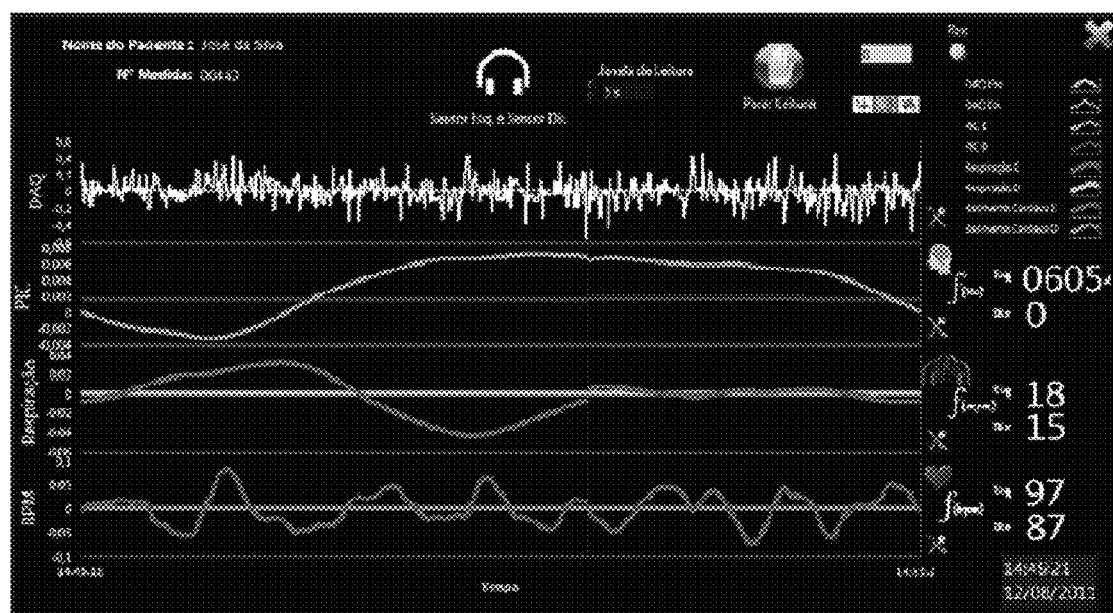
FIG. 18 is an illustrative embodiment of an intracranial pressure monitor display.

FIG. 18 illustrates a display 12/14 of raw data includes 34, 35, 36, and 37, during a real-time monitoring, in connection with other data output. This display also shows the heart and respiratory rate. (Display 12/14 can also be adapted to display the real-time curves, e.g., on the computer 21 display or, through an adapter, to a multiparametric monitor.)

Figure 19:
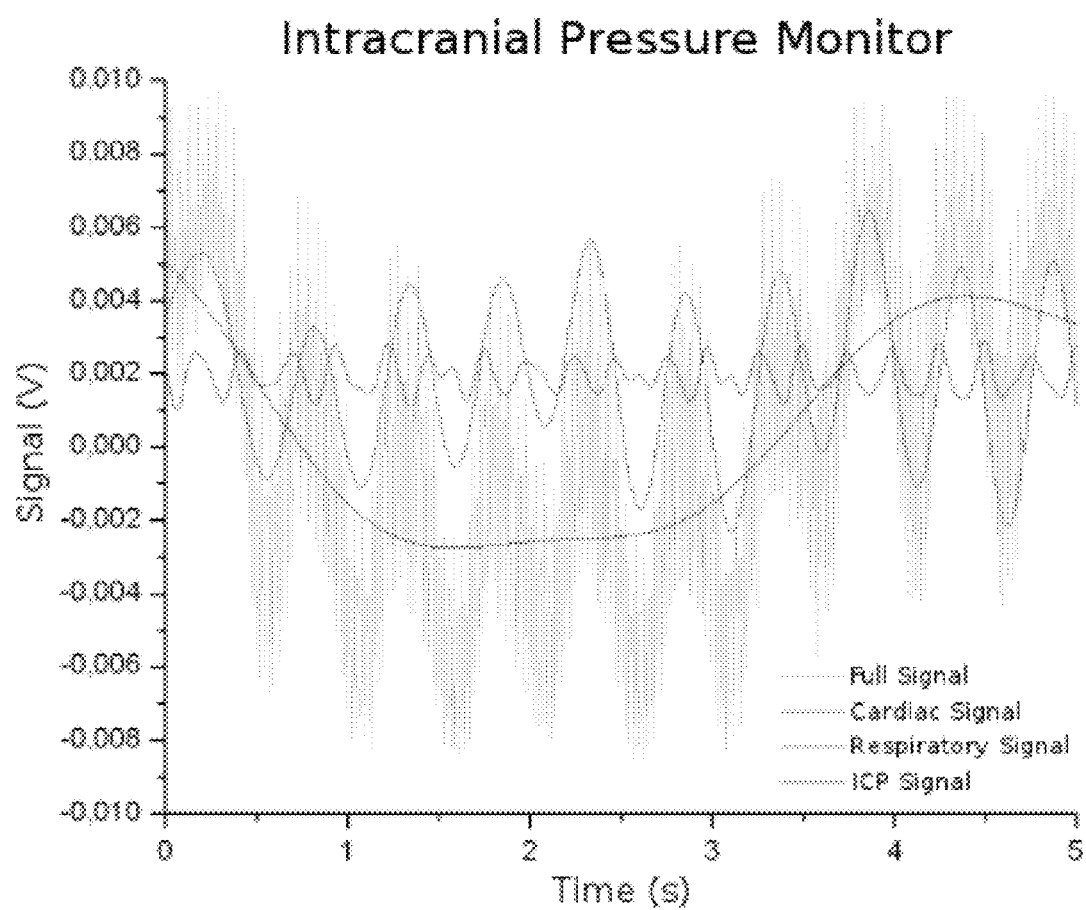
FIG. 19 is an illustrative embodiment of an intracranial pressure monitor signal display.

FIG. 19 illustrates the results of Fast Fourier filters 31 applied to the raw signal data, after the use of mathematical tools which divide the signal data into the ICP 35, cardiac data 36, and respiratory 37 data.

Embodiments herein can, therefore, include the non-invasive equipment, or parts thereof or operably associated therewith, and methods to detect intracranial pressure (ICP) and use the detected ICP and related data. Any of this data can be processed and analyzed, for medical, pathological, and/or physiological situations, for diagnosis and treatment responsive to the detecting and output from the detecting, especially to identify an initial condition, identify how a patient is responding to a treatment and/or how to adjust a subsequent treatment based on the patient's detected reaction to the treatment, and when to cease the treatment because a target condition has been detected. This has application in the diagnoses of one or more pathologies, e.g., in the vascular, cardiac, respiratory, and central nervous system disorders, and responses to administrations of treatment.

Figure 20:
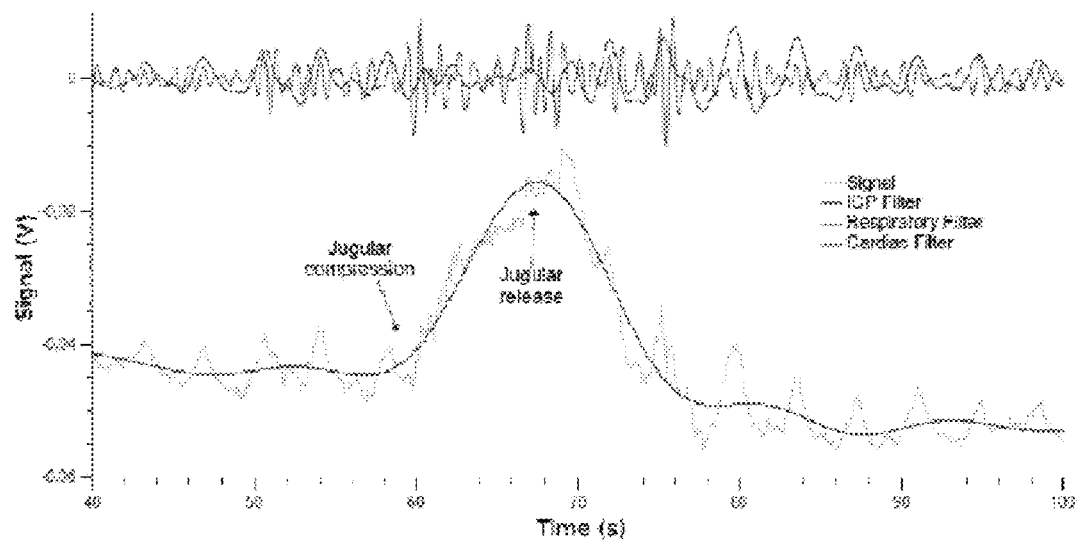
FIG. 20 is an illustrative embodiment of a display of intracranial pressure monitoring of a jugular maneuver.

To exemplify the foregoing, a display, e.g., display 14, is presented in FIG. 20 to illustrate the variation of physiologic parameters during a jugular compression. FIG. 20 illustrates a baseline to the left of the peaks on the lower curves, a peak that illustrates an abnormality associated with jugular blood flow, and after administration of a treatment, a return to normal ranges, suggesting that further or alternative treatment is not needed or that the treatment has been sufficient. This is an example of the behavior of intracranial pressure in situations such as hemorrhagic stroke (increase of pressure—jugular compression) and the return (after jugular release) to baseline after treatment (e.g., decompressive craniotomy). The ICP value returns below the baseline, due to the body's defense mechanisms, which tries to maintain body's homeostasis by activating defense mechanisms.

Figure 21:
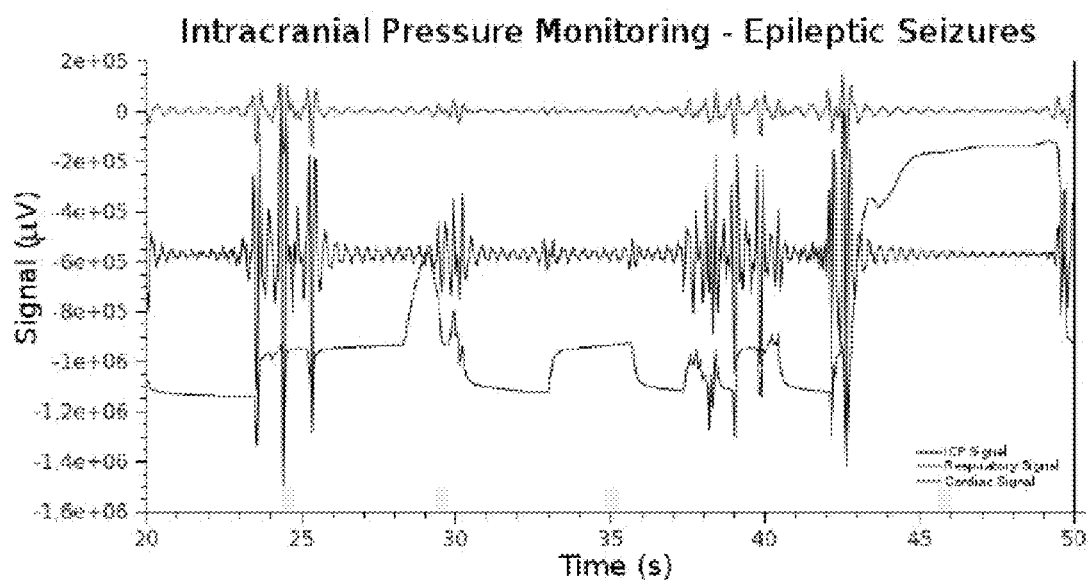
FIG. 21 is an illustrative embodiment of a display of intracranial pressure monitoring of epileptic seizures.

In another teaching embodiment, detection of epilepsy seizures in Wistar rats is illustrated in FIG. 21. FIG. 21 illustrates detecting and diagnostics for the seizures (above reference squares added to the bottom axis of the display) and the detected the physiological parameters. The output signals illustrate an epileptic's aura, the sign before the external symptoms. These results show variations in cardiologic, respiratory and ICP signals, monitored inside the skull. Variations in these signals may collaborate diagnosis and treatment monitoring of epileptic patients.

Figure 22:
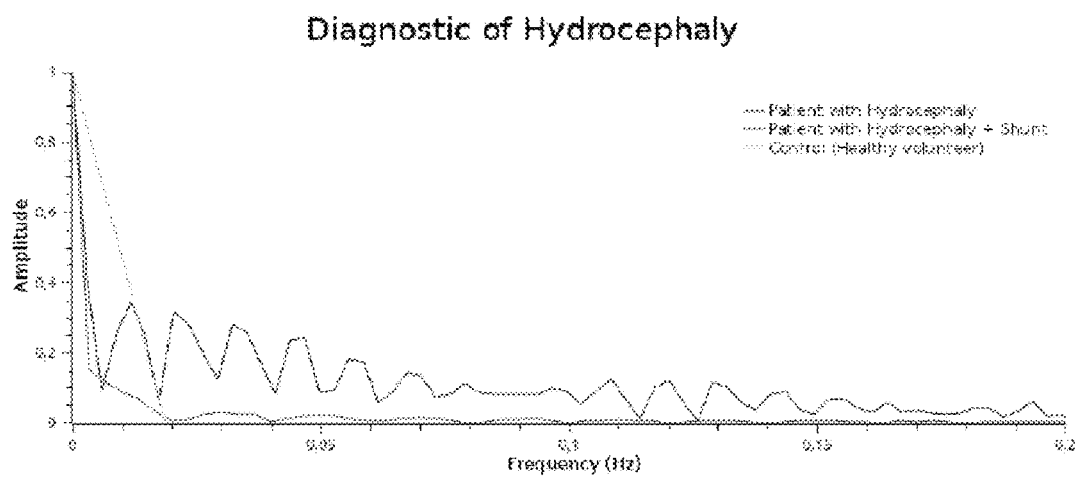
FIG. 22 is an illustrative embodiment of a display of diagnostic of hydrocephaly.

In another teaching embodiment, the equipment 1 can be used in the diagnostics of hydrocephaly, and to check for proper operation of the shunts. FIG. 22 shows the results of the equipment 1 monitoring illustrative of hydrocephaly patients.

Hydrocephalus is a disease diagnosed using imaging techniques; these devices are expensive and not available for the entire population. The equipment presented here is able to indicate a diagnosis of hydrocephalus through the analysis of low frequency waves on ICP (0 to 0.2 Hz), which vary greatly in amplitude in patients with hydrocephalus, as shown in FIG. 22. It's possible see in this graph that patients after insertion of shunts show a decrease in the amplitude of these oscillations. An appropriate periodic monitoring routine now is possible with the equipment described herein.

In still another teaching embodiment, the sensor 15 and processing related thereto can detect and/or monitor the real-time drug effects, e.g., to determine the dosage and effect, the drug absorption, etc. In some embodiments, especially in children, in old age and patients require drug multi-therapy, and the detecting can be used to determine treatment, e.g., administer more of one or another medication, and determine, from the detected response of the patient, whether to adjust or cease the treatment, etc. For example, drugs can decrease the metabolism, or physiological parameters such as blood pressure, resulting in an intracranial pressure decrease that is detectable according to embodiments herein. Similarly, the reverse effect can be observed in drugs that raise blood pressure or body metabolism.

Monitoring of drugs can be exemplified in the three cases described below.

Figure 23:
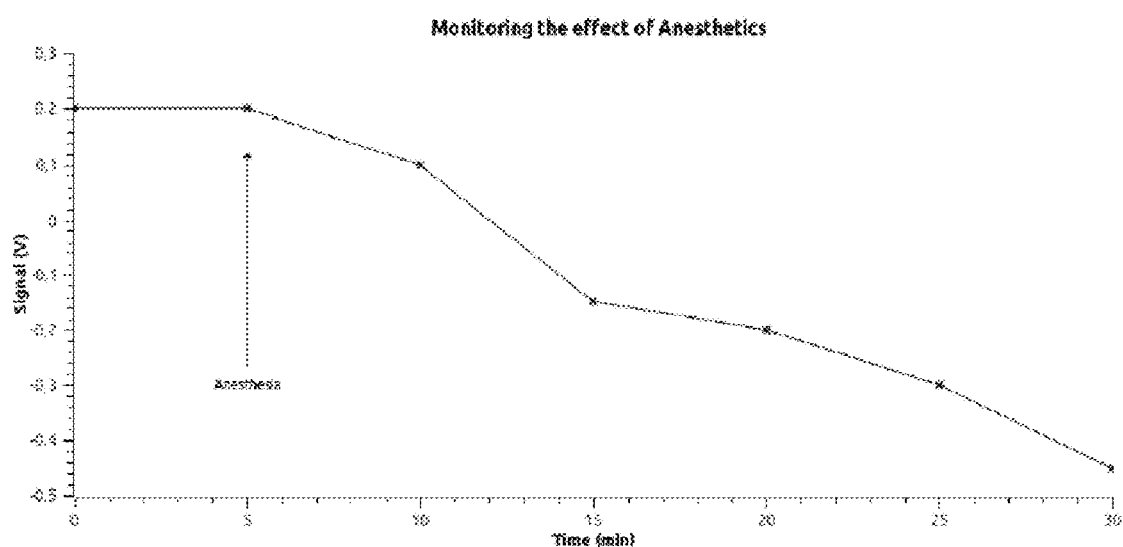
FIG. 23 is an illustrative embodiment of a display with respect to an intravenous use of Sodium Thiopental in pigs.

The FIG. 23 illustrates a display, e.g., display 12 and/or display 14, with respect to an intravenous use of Sodium Thiopental in pigs with 4 Kg (dosage=7 mg/kg body weight), a barbiturate general anesthetic. The FIG. 23 illustrates a decrease in intracranial pressure after the use of this anesthetic (black arrow), thereby illustrating how the sensor 15 and processing related thereto can detect and/or monitor in connection with anesthesia, important information during surgical procedures.

FIG. 23 is illustrative of detecting and/or monitoring of the depth of anesthesia, e.g., on a patient. A black arrow inserted into FIG. 23 shows the use of Sodium Thiopental.

Dipyrone is an analgesic. The decrease in blood pressure caused by this drug can be the subject of the sensor 15 and processing related thereto, e.g., with respect to ICP. In FIG.

24 a display, e.g., display 12 and/or display 14, with respect to rats with approximately 300 g, are illustrated as having received dipyrone by gavage (5 mg/kg body weight). The detecting and/or monitoring, in real time, of the action of the drugs is illustrative of maintenance of patients in intensive care units. Accordingly, embodiments herein can be configured and used to increasing, decrease, supplement, or cease administration of one or more pharmaceuticals or other treatments.

Figure 24:
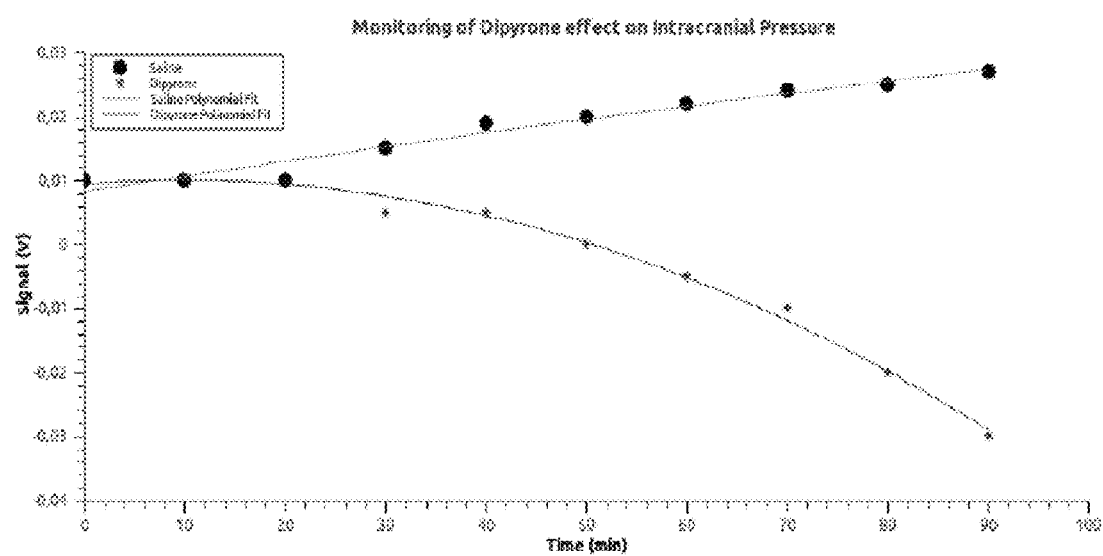
FIG. 24 is an illustrative embodiment of a display with respect to rats having received dipyrone.

FIG. 24 is illustrative of detecting and/or monitoring the effect of dipyrone, e.g., on a patient. Decreased intracranial pressure detected or monitored after the injection of analgesic.

There are substances that can increase the metabolism and the patient's blood pressure, such as adrenaline. The detecting and/or monitoring the effect of such drugs on a patient can be implemented with respect to maintaining of patient's homeostasis, and embodiments herein, are accordingly illustrated in FIG. 25 (rats with 300 g, adrenaline dosage of 0.01 mg/Kg body weight). Accordingly, this effect can be detected or monitored via the sensor 15 and processing related thereto, e.g., with respect to ICPICP, as illustrated in the FIG. 25 display, e.g., display 12 and/or display 14.

Figure 25:
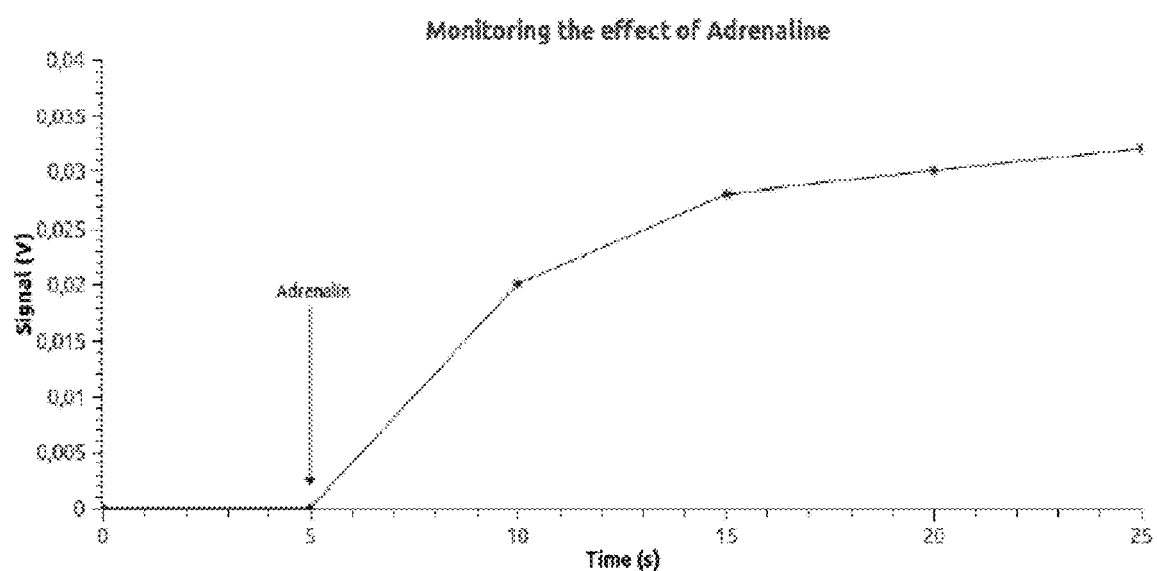
FIG. 25 is an illustrative embodiment of a display with respect to a response to adrenaline.

FIG. 25 is illustrative of detecting and/or monitoring a response to adrenaline, e.g., in a patient. The black arrow indicates the injection of the drug.

Figure 26:
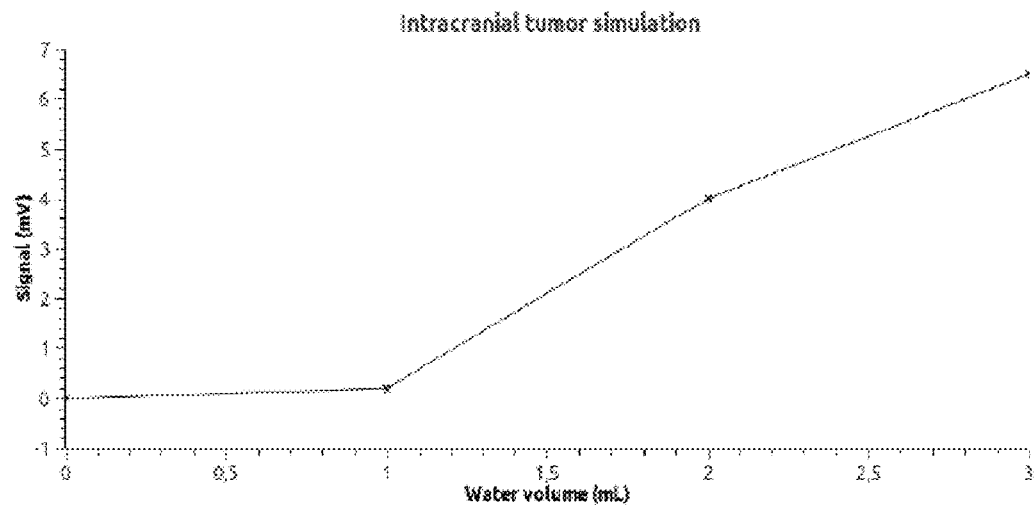
FIG. 26 is an illustrative embodiment of a display with respect to an intracranial tumor.
Figure 27:
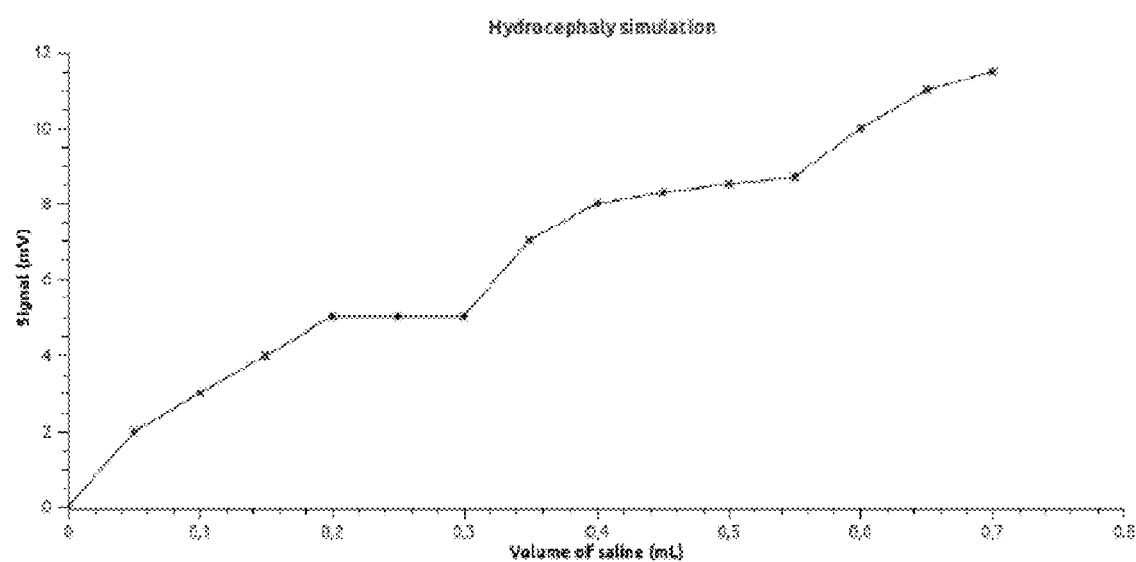
FIG. 27 is an illustrative embodiment of a display with respect to hydrocephaly and evaluating the performance of shunts.

The sensor 15 and processing related thereto, e.g., with respect to ICP. In FIGS. 26 and 27, each show a display, e.g., display 12 and/or display 14, with respect to diagnosing and monitoring diseases such as intracranial tumors, hydrocephalus, and others previously discussed herein, as well as in processes in which detections of a patient are used to determine treatment of the patient, e.g., by detected patient response to the treatment. FIGS. 26 and 27 illustrate a diagnosis simulated with respect to animal experimentation.

FIG. 26 is illustrative of (via a simulation) of intracranial tumor in rabbits (1.5 kg). For example, a rubber balloon can be inserted into the subdural space, the balloon connected to a cannula, so as to be able to inflate the balloon, e.g., with water. The FIG. 26 display, e.g., display 12 and/or display 14, is illustrated as monitoring or detecting changes due to the increase in the balloon, which represents a tumor growth. This teaching illustration is provided to indicate the ability to diagnose and monitor disease progression, as well as the efficacy of treatments such as chemotherapy and radiotherapy.

FIG. 26 provides a tumor simulation, e.g., in a patient.

Another teaching embodiment is directed to diagnosing hydrocephaly and evaluating the performance of shunts. The FIG. 27 display, e.g., display 12 and/or display 14, is illustrated as detecting and/or monitoring of the disease by an experimental animal model (rats with 300 g) in which rats received saline injection into the spinal canal, thus simulating the accumulation of cerebrospinal fluid, characteristic of this disease. The display in FIG. 27 is illustrated as showing in real time the increase in intracranial pressure resulting from this volume variation, e.g., in a patient.

FIG. 27 provides a hydrocephaly simulation. Depending on the embodiment for the desired application, the sensor 15 and processing related thereto, can be configured and used to detect and/or monitor the intracranial pressure in patients with trauma, hydrocephaly, tumors, epilepsy, stroke, etc. so as to produce diagnostic data related to the corresponding medical condition and/or to produce data corresponding to a patient's reaction to treatment of that condition, e.g., so as to adjust the treatment responsive to what is detected. (Note that embodiments are not limited to human patient embodiments, and thus can include embodiments configured for animals, especially in connection with veterinary medicine and surgery.) Other examples include hydrocephaly diagnoses, and evaluating the functioning of hydrocephaly shunts, edemas, chronic pain, migraine, etc. (e.g., to evaluate the action of drugs and their half-life in the patient's brain). Still further examples include diagnostics and treatment of brain symptoms related to cerebral fluid flow, labyrinthits, nausea, secondary injury, and treatment thereof. And treatment can, for example, include administering medication, surgery, etc., in connection with the data or display or other output indicating a patient condition and response to the treatment.

FIG. 28 is an illustrative embodiment of a display with respect to ICPNI Monitoring. The ICP wave has typical morphological characteristics, this wave is composed by P1 that is the result of the systolic wave of arterial blood pressure, P2 that is consequence of the cardiac valve closure and P3 that show the accommodation of blood pressure wave in the central nervous system.

Additional examples include diagnosing proper operation of a stent, analyzing cardiac and respiratory parameters with respect to the central nervous system, analyzing cardiologic, respiratory, cardiac and vascular parameters using maneuvers (postural changes, jugular compress, valsava maneuver and physical activity), etc.

Yet further examples include diagnostics and analyses of time series of the intracranial pressure, e.g., to determine the drug dosage required for the adequate homeostasis of the brain pressure. Additional examples include pharmaceutical clinical trials, detecting/monitoring/evaluating the depth of anesthesia procedures in general surgery and making adjustments thereto in response to the data. Yet still further examples include detecting or monitoring the efficiency of chemotherapy and radiotherapy in intracranial and/or skull tumors, cardiologic, and respiratory analyses related to the intracranial pressure signal, etc. and treatment adjustments in response to what is detected.

Other embodiments can similarly be configured for producing the data in connection with exercise physiology, gymnastics, etc. to monitor the effect of physical activity in the brain.

Due to the non-invasive aspects of embodiments herein, the detecting or monitoring can be carried out with respect to cases of loss consciousness (syncope) during space and flight situations, or in cases of pressure changes, such as divers, climbers or other activities with pressure changes.

In sum, appreciation is requested for the robust range of possibilities flowing from the core teaching herein. More broadly, however, the terms and expressions which have been employed herein are used as terms of teaching and not of limitation, and there is no intention, in the use of such terms and expressions, of excluding equivalents of the features shown and described, or portions thereof, it being recognized that various modifications are possible within the scope of the embodiments contemplated and suggested herein. Further, various embodiments are as described and suggested herein. Although the disclosure herein has been described with reference to specific embodiments, the disclosures are intended to be illustrative and are not intended to be limiting. Various modifications and applications may occur to those skilled in the art without departing from the true spirit and scope defined herein.

Thus, although illustrative embodiments have been described in detail above, it is respectfully requested that appreciation be given for the modifications that can be made based on the exemplary embodiments, implementations, and variations, without materially departing from the novel teachings and advantages herein. Accordingly, such modifications are intended to be included within the scope defined by claims. In the claims, and otherwise herein, means-plus-function language is intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment fastening wooden parts, a nail and a screw may be equivalent structures.

The invention claimed is:

1. A method to digitally produce and communicate intracranial pressure data from skull deformation electric signals, the method comprising:
   affixing at least one non-invasive skull deformation sensor having a pin that makes direct contact with a patient's head and that receives forces produced by skull deformation;
   communicating forces received by the pin through a cantilever bar to a transducer that converts the communicated forces into skull deformation electrical signals
   receiving, from at least one non-invasive skull deformation sensor, detected skull deformation electric signals at electrical equipment configured to transform and process the skull deformation signals that are received;
   transforming and processing, by the electrical equipment, the received skull deformation electric signals to produce digital intracranial pressure data; and
   outputting, by the electrical equipment, the digital intracranial pressure data via an output device operably associated with the electrical equipment to render the digital intracranial pressure data.

2. The method of claim 1, wherein the skull deformation electric signals are analog signals, and the electrical equipment includes an amplifier, an analog-to-digital converter, a processor, a memory, and a monitor, and wherein the transforming and processing includes:
   amplifying, by the amplifier, the skull deformation electric signals that are received from said at least one sensor to produce amplified analog skull deformation signals;
   converting, by the analog-to-digital converter, the amplified skull deformation signals from analog form into digital form skull deformation electric signals;
   applying, with said processor, a Fournier Transform, a Fast Fourier Transform, or both on the digital form skull deformation electric signals to produce the digital intracranial pressure data; and
   storing, in the memory, the digital intracranial pressure data in a database; and wherein the outputting includes displaying, on the monitor, the rendered digital intracranial pressure data.

3. The method of claim 1, further including producing the detected skull deformation electric signals with said at least one sensor noninvasively located with respect to a human or an animal.

4. The method of claim 1, wherein the transducer is an electric, magnetic, piezoelectric, optic, or mechanical transducer.

5. The method of claim 4, wherein said at least one sensor is noninvasively located by a strap, band, hat, or helmet.

6. The method of claim 4, wherein said at least one sensor is noninvasively located by an apparatus which substantially fixes a patient's position with respect to said at least one sensor.

7. The method of claim 1, wherein said at least one sensor comprises a plurality of sensors, and the transforming and processing, by the electrical equipment, the received skull deformation electric signals to produce the digital intracranial pressure data comprises transforming and processing, by the electrical equipment, the received skull deformation electric signals from said plurality of sensors.

8. The method of claim 1, wherein the output device displays the rendered digital intracranial pressure data.

9. The method of claim 1, wherein the digital intracranial pressure data includes an intracranial pressure signal, a respiratory signal and frequency, and cardiac signal and frequency data.

10. The method of claim 1, further including producing, from the intracranial pressure data, real-time curves of physiological parameters; and wherein the outputting includes displaying the curves by the output device.

11. The method of claim 10, wherein the real-time curves of the physiological parameters include curves of at least two of intracranial pressure, respiratory cycles, and cardiac cycles.

12. The method of claim 10, wherein the real-time curves of the physiological parameters include curves of intracranial pressure, respiratory cycles, and cardiac cycles.

13. The method of claim 1, wherein the digital intracranial pressure data includes data showing changes in the intracranial pressure.

14. The method of claim 1, wherein the digital intracranial pressure data includes data showing an abnormality in a wave morphology corresponding to changes in the intracranial pressure.

15. The method of claim 1, wherein the transforming and processing includes performing mathematical analyses using signal analysis and pattern recognition sufficient to show an abnormality in wave morphology.

16. The method of claim 1, further including communicating at least some of the digital intracranial pressure data such that said at least some of the digital intracranial pressure data is digitally inserted into a report or medical record preconfigured in association with one or more of neurological, physiological, pathological, pharmacological, psychological, and endocrinological data.

17. The method of claim 1, further including communicating at least some of the digital intracranial pressure data such that said at least some of the digital intracranial pressure data is digitally inserted into a medical record in association with one or more of neurological, physiological, pathological, pharmacological, and endocrinological data, and further in association with patient data.

18. The method of claim 1, further including communicating at least some of said output such that at least some of the digital intracranial pressure data is digitally inserted into a medical record in association with data indicative of one or more of a trauma, a stroke, epilepsy, an intracranial hemorrhage, a hydrocephalus, a migraine headache, a headache, a tumor, a postural change, a cardiologic disease, a lie or falsehood, a neuroparasitosis, cystocercosis, craniosynostosis, hydrocephalus, a jugular blood flow abnormality, a pharmacologically induced change in intracranial pressure, an anesthetic, an analgesic, a hormone, a dynamical effect of a neurologic actives drug, a dynamical effect of a disease, an onset of ictus of a seizure, a ventricle-peritoneal shunt problem, a lumbar puncture, a brain death.

19. The method of claim 1, further including communicating at least some of said output such that at least some of the digital intracranial pressure data is digitally inserted into a medical record in association with a diagnosis.

20. The method of claim 1, further including communicating at least some of said output such that at least some of the digital intracranial pressure data is digitally inserted into a medical record in association with data indicative of one or more of a diagnosis, a treatment, a treatment adjustment, and a treatment cessation.

21. The method of claim 20, wherein said least some of the digital intracranial pressure data, indicative of one or more of a diagnosis, a treatment, a treatment adjustment, and a treatment cessation, comprises data indicative of a stroke.

22. The method of claim 20, wherein said least some of the digital intracranial pressure data, indicative of one or more of a diagnosis, a treatment, a treatment adjustment, and a treatment cessation, comprises data indicative of a seizure.

23. The method of claim 20, wherein said least some of the digital intracranial pressure data, indicative of one or more of a diagnosis, a treatment, a treatment adjustment, and a treatment cessation, comprises data indicative of hydrocephaly.

24. The method of claim 1, further including communicating at least some of said output such that at least some of the digital intracranial pressure data is digitally inserted into a medical record in association with data indicative of a drug effect.

25. The method of claim 1, further including communicating at least some of said output such that at least some of the digital intracranial pressure data is digitally inserted into a medical record in association with data indicative of an anesthetic.

26. The method of claim 1, further including communicating at least some of said output such that at least some of the digital intracranial pressure data is digitally inserted into a medical record in association with data indicative of an analgesic.

27. The method of claim 1, further including communicating at least some of said output such that at least some of the digital intracranial pressure data is digitally inserted into a medical record in association with data indicative of a hormone.

28. The method of claim 1, further including communicating at least some of said output such that at least some of the digital intracranial pressure data is digitally inserted into a medical record in association with data indicative of a tumor.

29. The method of claim 1, further including communicating at least some of said output such that at least some of the digital intracranial pressure data is digitally inserted into a report or medical record in association with data indicative of an evaluation of one or more of physiology of: exercise, a shock to a head, a rapid acceleration or deceleration, microgravity, a pilot's intracranial pressure during flying, an effect of an explosion or shock wave, a physiologic parameter associated with temperature, and a physiologic parameter associated with humidity.

30. The method of claim 1, further including communicating at least some of said output such that at least some of the digital intracranial pressure data is digitally inserted into a report or medical record in association with data indicative of a spinal puncture technique.

31. The method of claim 1, further including communicating at least some of said output such that at least some of the digital intracranial pressure data is digitally inserted into a report or medical record in association with data indicative of a clinical trial.

32. The method of claim 1, further including communicating at least some of said output such that at least some of the digital intracranial pressure data is digitally inserted into a report in association with data indicative of an animal.

33. The method of claim 1, further including communicating at least some of said output such that at least some of the digital intracranial pressure data is digitally inserted into a report or medical record in association with data indicative of a human.

34. The method of claim 1, further including communicating at least some of said output such that at least some of the digital intracranial pressure data is digitally inserted into a report in association with data indicative of training.

35. The method of claim 1, further including communicating at least some of said output such that at least some of the digital intracranial pressure data is communicated to a digital device remote from a medical facility where the electrical equipment is located.

36. The method of claim 1, further including communicating at least some of said output such that at least some of the digital intracranial pressure data is digitally inserted into a report or medical record which is replayed to a digital device remote from a medical facility where the electrical equipment is located.

37. The method of claim 1, further including monitoring the digital intracranial pressure data for a threshold, such that if the threshold is encountered, an alarm is triggered.

38. A method to digitally produce and communicate intracranial pressure data from skull deformation electric signals bearing intracranial pressure information combined with cardiac and respiratory influences according to claim 1,
wherein the transforming and processing is performed by converting the skull deformation electrical signals into digital form skull deformation electric signals, and by using a programmed processor that applies a Fourier Transform, a Fast Fourier Transform, or both on the digital form skull deformation electric signals to produce the digital intracranial pressure data by extracting the digital intracranial pressure data while excluding cardiac and respiratory influences on the basis of frequency; and
storing the digital intracranial pressure data in a memory operably associated with the processor.

* * * * *